US009427336B2

(12) United States Patent
Axelson, Jr. et al.

(10) Patent No.: US 9,427,336 B2
(45) Date of Patent: Aug. 30, 2016

(54) INTRAOPERATIVE DYNAMIC TRIALING

(71) Applicant: Stryker Corporation, Kalamazoo, MI (US)

(72) Inventors: Stuart L. Axelson, Jr., Succasunna, NJ (US); Emily Hampp, Far Hills, NJ (US); John R. Fossez, Frisco, TX (US)

(73) Assignee: Stryker Corporation, Kalamazoo, MI (US)

( * ) Notice: Subject to any disclaimer, the term of this patent is extended or adjusted under 35 U.S.C. 154(b) by 217 days.

(21) Appl. No.: 13/974,584

(22) Filed: Aug. 23, 2013

(65) Prior Publication Data

US 2015/0057758 A1 Feb. 26, 2015

(51) Int. Cl.
| | |
|---|---|
| *A61B 17/15* | (2006.01) |
| *A61F 2/46* | (2006.01) |
| *A61B 17/02* | (2006.01) |
| *A61F 2/38* | (2006.01) |
| *A61B 17/00* | (2006.01) |

(52) U.S. Cl.
CPC ............ *A61F 2/4684* (2013.01); *A61B 17/025* (2013.01); *A61B 17/154* (2013.01); *A61B 17/155* (2013.01); *A61B 17/00234* (2013.01); *A61B 17/157* (2013.01); *A61B 2017/00557* (2013.01); *A61B 2017/0268* (2013.01); *A61F 2/389* (2013.01); *A61F 2/3859* (2013.01); *A61F 2002/3895* (2013.01)

(58) Field of Classification Search
CPC .. A61B 17/154; A61B 17/155; A61F 2/3859
See application file for complete search history.

(56) References Cited

U.S. PATENT DOCUMENTS

| | | | | |
|---|---|---|---|---|
| 4,193,140 A | * | 3/1980 | Treace | ........................ 623/20.14 |
| 5,062,852 A | * | 11/1991 | Dorr et al. | ................. 623/20.33 |
| 5,464,406 A | | 11/1995 | Ritter et al. | |
| 5,470,354 A | | 11/1995 | Hershberger et al. | |
| 5,682,886 A | * | 11/1997 | Delp et al. | ..................... 600/407 |
| 5,733,290 A | * | 3/1998 | McCue et al. | ............... 606/86 R |

(Continued)

FOREIGN PATENT DOCUMENTS

WO 2006/136836 A2 12/2006

OTHER PUBLICATIONS

Written Opinion of the International Preliminary Examining Authority for Appln. No. PCT/US2014/052097 dated Oct. 19, 2015.

*Primary Examiner* — Nicholas Woodall
(74) *Attorney, Agent, or Firm* — Lerner, David, Littenberg, Krumholz & Mentlik, LLP

(57) ABSTRACT

A dynamic trialing method generally allows a surgeon to perform a preliminary bone resection on the distal femur according to a curved or planar resection profile. With the curved resection profile, the distal-posterior femoral condyles may act as a femoral trial component after the preliminary bone resection. This may eliminate the need for a separate femoral trial component, reducing the cost and complexity of surgery. With the planar resection profile, shims or skid-like inserts that correlate to the distal-posterior condyles of the final insert may be attached to the distal femur after the preliminary bone resection to facilitate intraoperative trialing. The method and related components may also provide the ability of a surgeon to perform iterative intraoperative kinematic analysis and gap balancing, providing the surgeon the ability to perform necessary ligament and/or other soft tissue releases and fine tune the final implant positions based on data acquired during the surgery.

28 Claims, 24 Drawing Sheets

(56) References Cited

U.S. PATENT DOCUMENTS

| | | |
|---|---|---|
| 5,735,904 A | 4/1998 | Pappas |
| 6,022,377 A | 2/2000 | Nuelle et al. |
| 6,077,270 A | 6/2000 | Katz |
| 6,575,980 B1 | 6/2003 | Robie et al. |
| 6,859,661 B2 | 2/2005 | Tuke |
| 7,066,961 B2 | 6/2006 | Michelson |
| 7,442,196 B2 | 10/2008 | Fisher et al. |
| 7,615,055 B2 | 11/2009 | DiSilvestro |
| 7,842,092 B2 | 11/2010 | Otto et al. |
| 8,197,489 B2 | 6/2012 | Chessar et al. |
| 8,603,101 B2 | 12/2013 | Claypool et al. |
| 2010/0010635 A1 | 1/2010 | Straszheim-Morley et al. |
| 2011/0015749 A1 | 1/2011 | Engh et al. |

\* cited by examiner

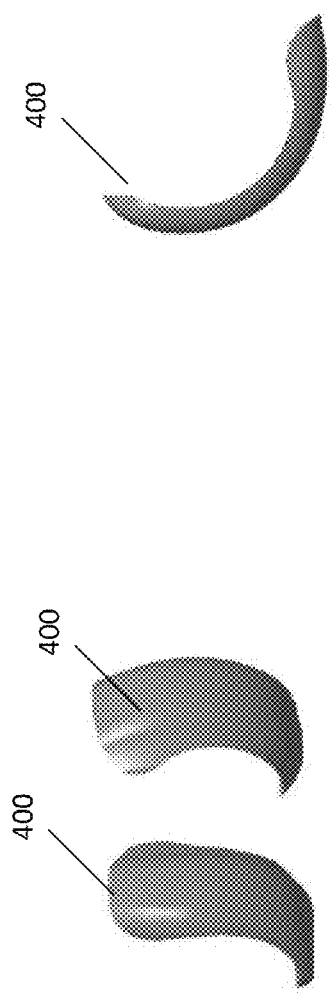
FIG. 8A
FIG. 8B
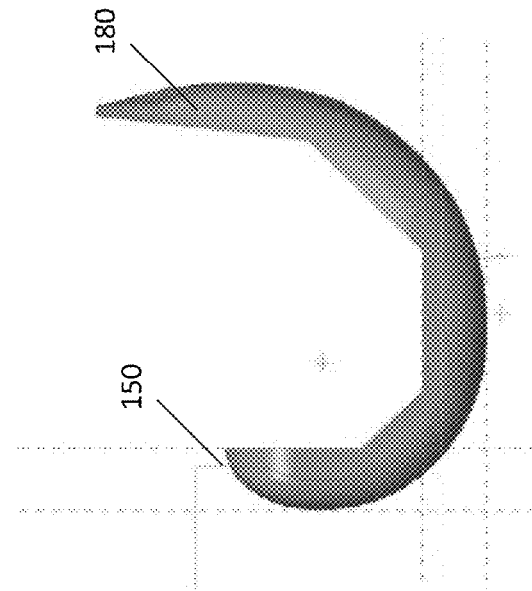
FIG. 8D
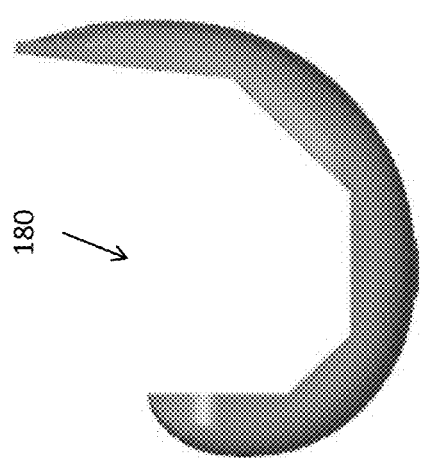
FIG. 8C

INTRAOPERATIVE DYNAMIC TRIALING

FIELD OF THE INVENTION

The present invention relates to trialing apparatus and methods in joint replacement procedures and in particular relates to intraoperative dynamic trialing using preliminary bone preparations determined according to a preoperative plan that correlates to the position and orientation of preoperatively planned final resections or resurfacings prior to implanting one or more joint prostheses.

BACKGROUND OF THE INVENTION

Knee joint replacement procedures generally include preparation and resurfacing of the femur, tibia and/or patella. Briefly, the surgical procedure may involve calculated bone resections of each bone with the goal of replacing damaged articular cartilage, restoring the joint line and returning the patient to a pain-free movement of the knee joint.

In order to ensure proper knee joint kinematics, trial components of the femur, tibia and/or patella may be used intraoperatively. During the surgery, each bone is resected and the trial components are placed on each respective bone to allow the surgeon to trial the joint through a full range of motion. During trialing, the surgeon generally assesses the joint line, range of motion and ligament tension. Trial components generally represent various thicknesses, widths, or profiles to replicate the final implant prosthesis. The trialing process allows the surgeon to ensure proper knee joint function prior to the implantation of the final prosthesis.

Current methods of trialing and resecting the femur and tibia may leave the surgeon with little or no flexibility in modifying the final bone resections following trialing the implant components. For example, if the bones are resected according to a final plan, and during trialing the surgeon finds non-optimal joint kinematics, it may not be possible to make additional bone resections to optimize the kinematics. Rather, the surgeon may only be left with limited options, for example performing ligament releases, to attempt to optimize joint kinematics while remaining "stuck" with the bones resected according to the final plan. Further, the more components that are involved in trialing procedures generally translates to higher cost, greater complexity, and increased duration of the trialing procedure. There exists a need for new apparatus and methods to simplify the trialing procedure and to allow a surgeon to perform intraoperative dynamic trialing such that information gained during trialing may be applied to modify the final planned bone resections.

BRIEF SUMMARY OF THE INVENTION

A dynamic trialing method generally allows a surgeon to perform a preliminary bone resection on the distal femur according to a curved resection profile, a planar resection profile, or a combination thereof. With the curved resection profile, the distal-posterior femoral condyles may act as a femoral trial component after the preliminary bone resection. This may eliminate the need for a separate femoral trial component, reducing the cost and complexity of surgery. With the planar resection profile, shims or skid-like trials that correlate to the distal-posterior condyles of the final femoral implant may be attached to the distal femur after the preliminary bone resection to facilitate intraoperative trialing. The method and related components may also provide the ability of a surgeon to perform iterative, intraoperative kinematic analysis and gap balancing, providing the surgeon the ability to perform necessary ligament and/or other soft tissue releases and fine tune the final implant positions based on data acquired during the surgery. For example, by performing dynamic intraoperative kinematic analysis using trial components that articulate in a way that corresponds to the final implant design plan, a surgeon may be able to debride osteophytes, remove menisci, and clean out around the posterior capsule to assess the affect the soft-tissue envelope has on knee positional alignment. This may all be done prior to making the final implant resections, which the surgeon may choose to modify based on the results of the dynamic intraoperative trialing.

In one embodiment, a dynamic trialing method includes creating a bone model of a distal femur of a patient and determining a curved resection profile on the bone model offset from distal and posterior nonresected articular surfaces of the distal femur. The distal femur may be resected by making a preliminary resection along the curved resection profile such that a first area of bone is removed from the distal femur. The resected distal femur may be engaged to a tibial trial coupled to a resected proximal tibia. Intraoperative kinematic analysis may be performed by at least articulating the proximal tibia with respect to the distal femur.

The step of performing kinematic analysis may include performing intraoperative gap balancing. The dynamic trialing method may include making a subsequent resection of the distal femur such that a second area of bone is removed from the distal femur. The subsequent resection may include making planar bone resections corresponding to mating surfaces on a femoral implant. The subsequent resection may be performed according to a final design plan. Alternatively the subsequent resection may be performed according to a modified final design plan, the modified final design plan being determined, at least in part, based upon results of the kinematic analysis.

In one embodiment, the tibial trial may include a first condylar portion connected to a second condylar portion, the first and second condylar portions each having a groove corresponding to an articular dish of a tibial implant plateau. The tibial trial may include a tibial trial insert and a template, the tibial trial insert being removable from the template. The dynamic trialing method may further include the step of removing the tibial trial insert from the template and inserting an alternative modular tibial trial insert into the template.

In another embodiment, the tibial trial may include a first insert having a proximal surface and a distal surface and a second insert having a proximal surface. The proximal surface of the first insert may have two grooves corresponding to articular dishes of the tibial implant plateau. The first insert may have at least two pegs extending distally from the distal surface of the first insert and the second insert may have at least two holes on the proximal surface of the second insert, the at least two pegs being configured to be inserted into the at least two holes.

In a further embodiment, the tibial trial may include a tibial insert having a first condylar portion configured to mate with a first groove insert and a second condylar portion configured to mate with a second groove insert. The first and second groove inserts may each have an articulation surface corresponding to the articular dish of the tibial implant plateau.

In still a further embodiment, the dynamic trialing method may include the step of coupling first and second femoral shims to first and second condyles of the distal femur after the step of resecting the distal femur by making a preliminary resection. The first and second femoral shims may each have an articulation surface configured to match a shape of the femoral implant. The first and second femoral shims may each have a bone contacting surface with a peg extending therefrom, the pegs being configured to facilitate fixing the first and second femoral shims to the resected distal femur.

In another embodiment, the tibial trial may include a first condylar portion, a second condylar portion and at least one insert surface, the at least one insert surface being connected to at least one expandable component having a volume that may expand or contract and also being configured to remain at a constant pressure. The tibial trial may have exactly one insert surface and exactly one expandable component, the first and second condylar portions being connected to one another. Alternately, the tibial trial may have two insert surfaces and two expandable components, a first insert surface corresponding to a first expandable component and the first condylar portion, and a second insert surface corresponding to a second expandable component and a second condylar portion. The tibial trial may include a connecting member physically connecting the first condylar portion to the second condylar portion, the first expandable portion being fluidly isolated from the second expandable portion. At least one expandable component may be a bellows. At least one expandable component may be connected to a fluid source configured to pump air and/or fluid, e.g. saline, into the expandable component.

In another embodiment of the invention, a dynamic trialing method may include the step of creating a bone model of a distal femur of a patient and determining a preliminary resection profile on the bone model. The method may also include resecting the distal femur by making a preliminary resection along the preliminary resection profile such that a first area of bone is removed from the distal femur. The preliminary resection profile may be determined, at least in part, based on a feature of a final design plan of a femoral implant. The final design plan of the femoral implant may include a femoral implant flexion axis, and the preliminary resection profile may be based on the femoral implant flexion axis. The preliminary resection profile may include a flexion axis, the flexion axis of the preliminary resection profile being coaxial with the femoral implant flexion axis. The method may also include the step of performing intraoperative kinematic analysis by at least articulating the proximal tibia with respect to the distal femur, and may also include the step of performing intraoperative gap balancing.

BRIEF DESCRIPTION OF THE DRAWINGS

FIGS. 8A-B are perspective and side views of femoral shims.

FIG. 8C is a side view of one embodiment of a femoral implant.

FIG. 8D is a side view showing a relationship between a femoral implant and a femoral shim.

DETAILED DESCRIPTION

As used herein, the term "distal" means more distant from the heart and the term "proximal" means closer to the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body. Also, as used herein, the terms "resecting," "resurfacing," and "bone preparation" are intended to be interchangeable and generally refer to removing or reshaping bone.

Figure 1:
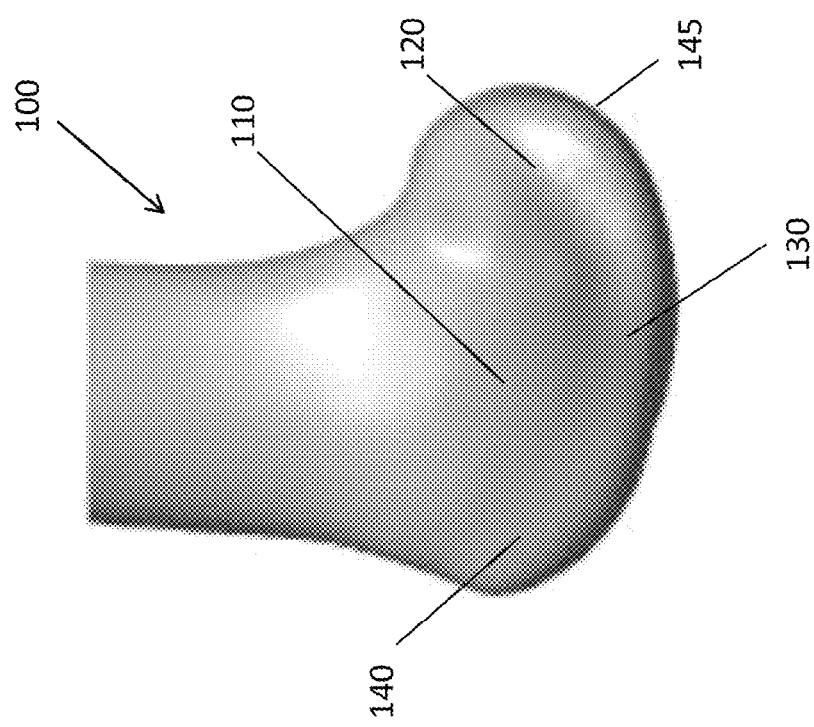
FIG. 1 is a side view of one embodiment of a non-resected distal femur.

FIG. 1 illustrates a distal portion of a non-resected distal femur 100 prior a knee replacement procedure. As illustrated, a first condyle 110 includes a posterior portion 120, a distal portion 130, and an anterior portion 140. Generally, in total knee arthroplasty ("TKA") procedures, up to five cuts are made to the distal femur 100, including distal, posterior, anterior, posterior chamfer, and anterior chamfer cuts. Following one or more of these cuts, a femoral trial component may be utilized with other trial components, for example a tibial trial component, to assess joint function prior to implanting a femoral prosthesis on the resected distal femur.

Figure 2:
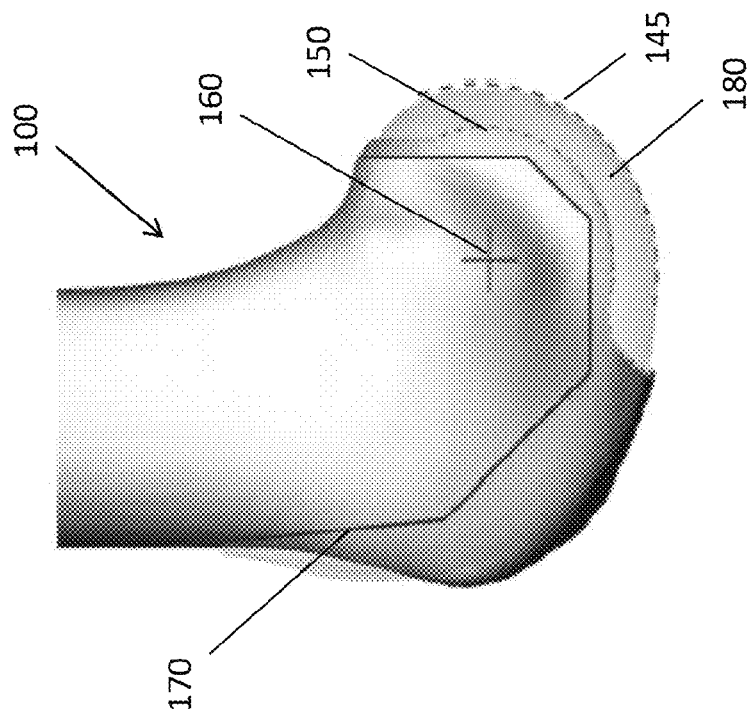
FIG. 2. is a side view of the distal femur of FIG. 1 including a curved line indicating a preliminary resection profile along with a plurality of planar lines indicating a final projected cut plan, including a final planned femoral implant position superimposed on the distal femur.

The distal femur 100 is illustrated in FIG. 2 after a preliminary bone preparation is made, outlined by broken line 150, to the posterior portion 120 and distal portion 130 of the distal femur 100. The preliminary bone preparation may take the form of a preliminary bone resection made along a preliminary resection profile 150. Although illustrated as substantially a curved resection profile, the preliminary resection profile may take the form of a planar resection profile, or a combination of a curved and planar resection profile. This preliminary bone resection along a curved resection profile of the distal femur 100 may be performed partly or fully by a robotic machining tool such as a rotating burr. The particular curved resection profile may be determined with the aid of a computer and may be determined based on a final implant design plan, including a flexion axis, for example, of a femoral implant 180 located in a desired position on distal femur 100. The computer may first be used to create a bone model of portions of the distal femur 100 to aid in the determination of the preliminary resection profile 150 and other operative plans. The preliminary resection profile 150 may be offset from distal and posterior nonresected articular surfaces of the distal femur 100, such as the posterior portion 120 of the distal femur. During the preliminary bone resection, a first area of the distal femur 100 is removed, represented by the difference between the articular surface 145 of non-resected distal femur 100 illustrated in FIG. 1 and the remaining portions up to the preliminary resection profile 150 illustrated in FIG. 2. The distance between the profile of articular surface 145 and preliminary resection profile 150 is approximately 4-5 mm along the length of each profile. Preferably, the preliminary resection profile 150 is planned such that, after the preliminary bone resection is made according to the curved resection profile, the curved surface of the prepared distal femur is coaxial with the final planned position of the femoral implant 180. That is, both share a common axis with the desired, preoperatively planned flexion axis 160, which is derived during preoperative planning. This provides a correlation between the final positional alignment of the femoral implant 180 and the resultant kinematics being assessed during trial reduction. The correlation may be determined regardless of whether, for example, a mechanical-classical or an anatomical alignment methodology is selected during the preoperative planning process. This may also provide the ability for the distal femur 100 itself to act as a trial for the femoral implant 180, described in more detail below.

The distal femur 100 in FIG. 2 is also superimposed with a final projected cut plan 170 representing the final planned distal, anterior, posterior, anterior chamfer and posterior chamfer cuts in the distal femur. As can be seen, the preliminary resection profile 150 may not interfere with the final projected cut plan 170. As described above, the preliminary bone resection removes between approximately 4 mm and approximately 5 mm of bone stock. It may also be preferred that the distance between the final projected cut plan 170 and the preliminary resection profile 150 along the articulating portion of the distal femur 100 is no more than between approximately 2 mm and approximately 3 mm. As is described in more detail below, this distance allows the surgeon to make small rotational and translational adjustments to the projected final cut plan 170 such that the actual final cuts vary slightly from those originally planned to account for information learned during trialing. This provides the surgeon with the ability to determine intraoperatively that modifications to the final projected cut plan 170, which modifications may include rotational and/or translational adjustments to the six degrees of freedom of the femoral implant 180, which are made to optimize joint kinematics, while still having enough bone remaining to perform additional resections to implement the modified final plan.

In certain embodiments described herein, a femoral implant 180 with a "single radius" may be used with the methods described herein, although other implants, such as an implant with a j-curve design, may also be used. Studies of kinematics and biomechanics have indicated that constant femoral condylar radii in natural knee motion are centered about the transepicondylar axis. Centering the radius of curvature about the transepicondylar axis provides ligament isometry, not only in full extension and 90 degrees of flexion, but through the entire range of motion. The surgical plan described above takes into account a femoral implant that is designed with a "single radius," as is shown and described, for example in U.S. Pat. No. 5,824,100, the disclosure of which is hereby incorporated by reference herein in its entirety. The single radius centered about the epicondylar axis reproduces natural knee movements designed to minimize the quadriceps forces required for extension thereby maximizing muscle efficiency. However, as is described below, benefits may still be obtained from performing intraoperative trialing after performing a preliminary bone resection corresponding to an implant that is not designed with a "single radius."

During preoperative planning, the distal femur 100 is additionally superimposed with a femoral implant 180 in phantom lines, the femoral implant being illustrated in a final position after the final cuts have been made to the distal femur 100. In one example, the distance between the flexion axis 160 and the outer surface of the femoral implant 180 are approximately equal along the portions of the femoral implant that articulate. Having a constant center of rotation or a single radius for both the distal femur 100 prepared according to the preliminary resection profile 150 and the femoral implant 180 allows for the distal femur itself to act as a trial for the femoral implant, eliminating the need for separate femoral trials. However, even with an alternative femoral implant that does not have a "single radius," the final position of the implant may be used to derive the proper planned position of the femoral component, usually in a measured resection position (as opposed to a flexion axis) which may be used to create an alternative preliminary resection profile. For example, an alternative preliminary resection profile may include a number of planar cuts as part of a planar resection profile, or a combination of planar and curved cuts. Apparatus discussed below may be attached to the distal femur after the preliminary bone resection, and intraoperative trialing corresponds to final implant kinematics may be performed.

Figure 3B:
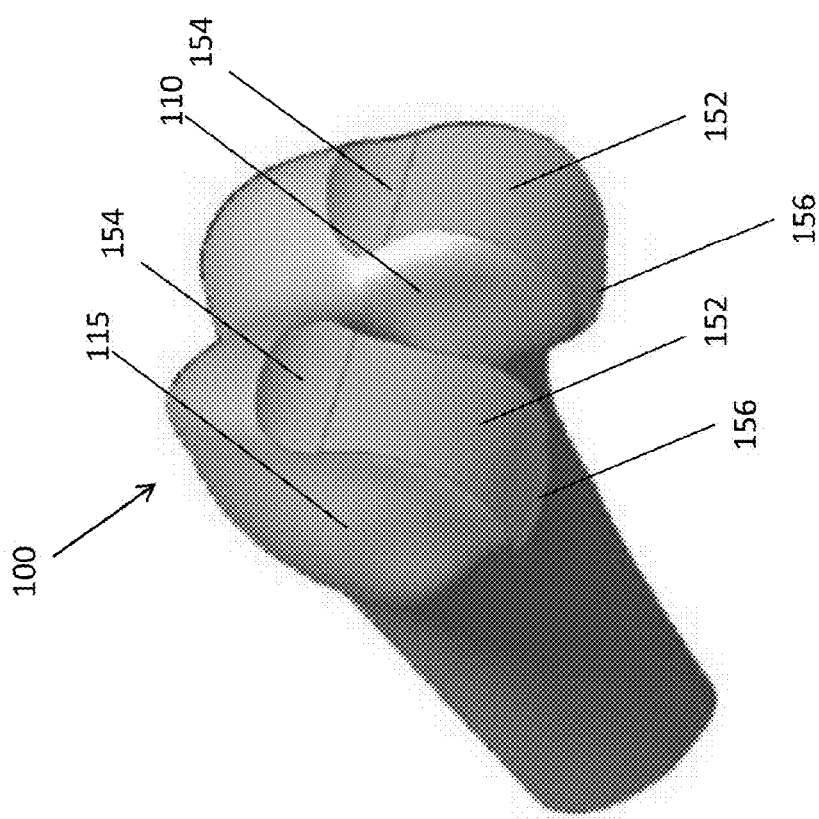
FIGS. 3A-C are side, perspective, and front views of the distal femur of FIG. 1 after a preliminary bone resection has been performed.
Figure 3A:
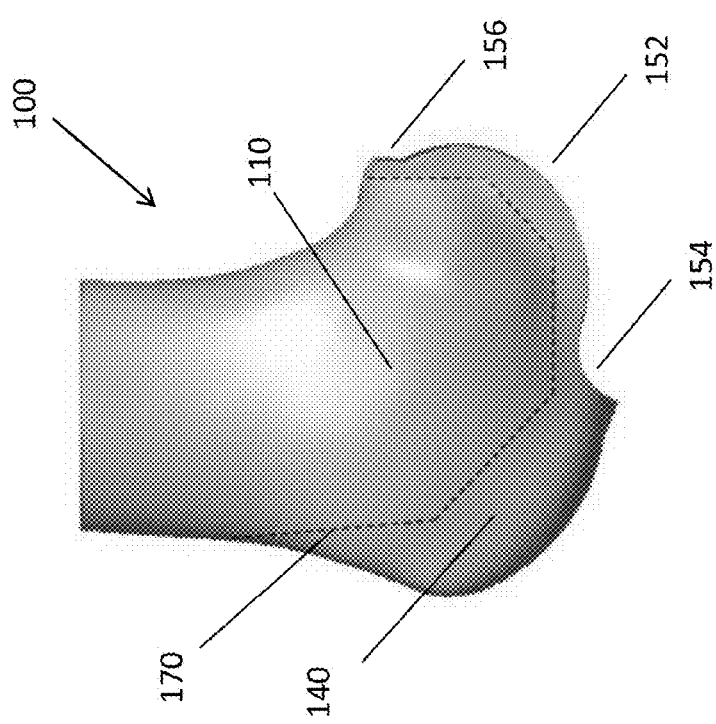
Figure 3D:
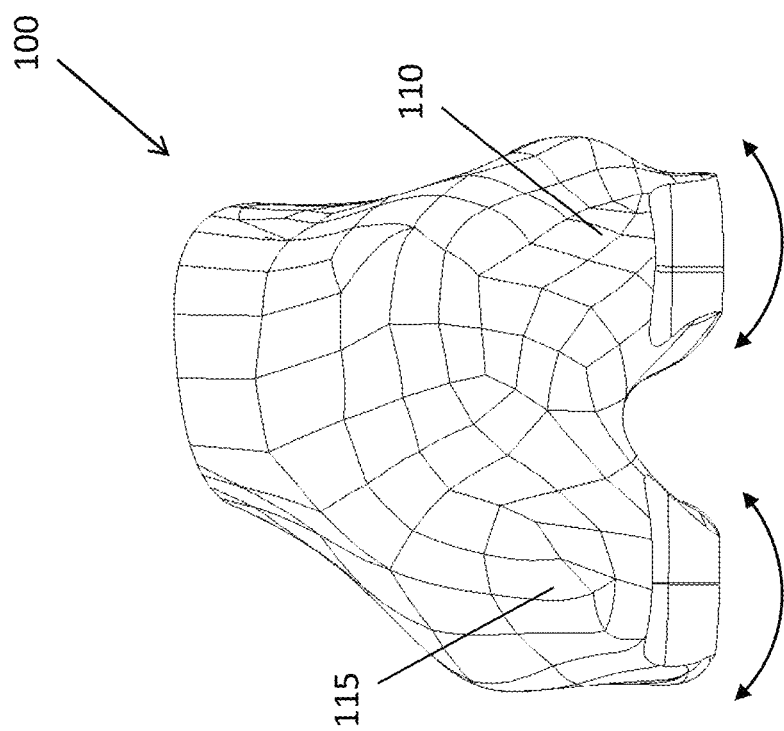
FIG. 3D is a front view of the distal femur of FIG. 1 after an alternate preliminary bone resection has been performed.
Figure 3C:
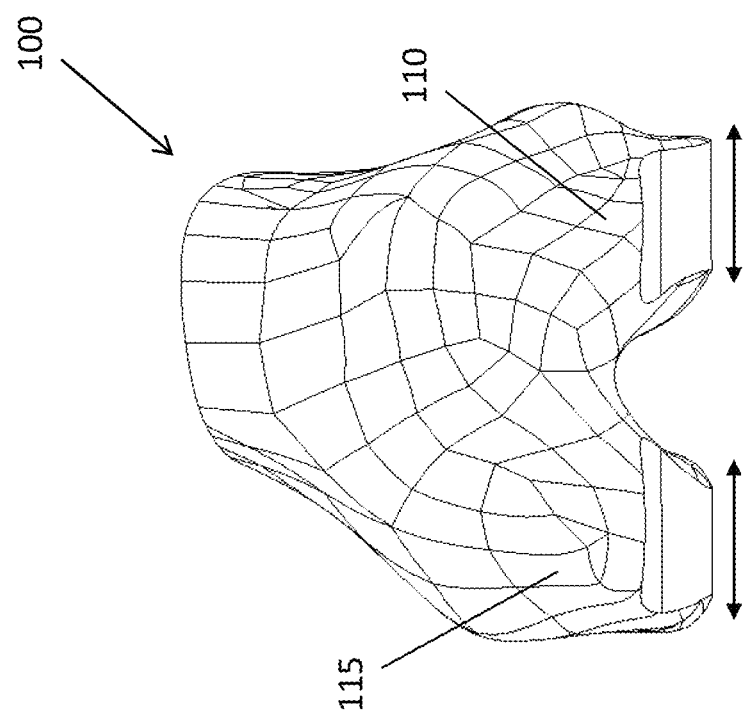

FIGS. 3A-B illustrate different views of the distal femur 100 after the preliminary bone resection is made according to the preliminary resection profile 150. FIG. 3A also illustrates the final projected cut plan 170 as a broken line. Using the illustrated plan, after the preliminary bone resection, the femoral condyles 110, 115, each have a rounded articulating surface 152 with a flexion axis that is coaxial with the flexion axis of the femoral implant when positioned according to the preoperative plan. In this embodiment, a first end of the rounded articulating surface 152 transitions into an anterior stop 154 and a second end of the rounded articulating surface 152 transitions into a posterior stop 156. FIG. 3C illustrates a front view of the distal femur 100 after the preliminary bone resection is made according to the preliminary resection profile 150. As can be seen, the condyles 110, 115 have a radius in the sagittal plan only, with the frontal plane of the condyles being relatively planar. However, as illustrated in FIG. 3D, an alternative preliminary bone resection according to an alternate preliminary resection profile may include machining the condyles 110, 115 so that they are curved in both the sagittal, coronal and transverse planes. This additional curvature may better accommodate rotation of the femur on the tibia during the dynamic trialing step.

Figure 4B:
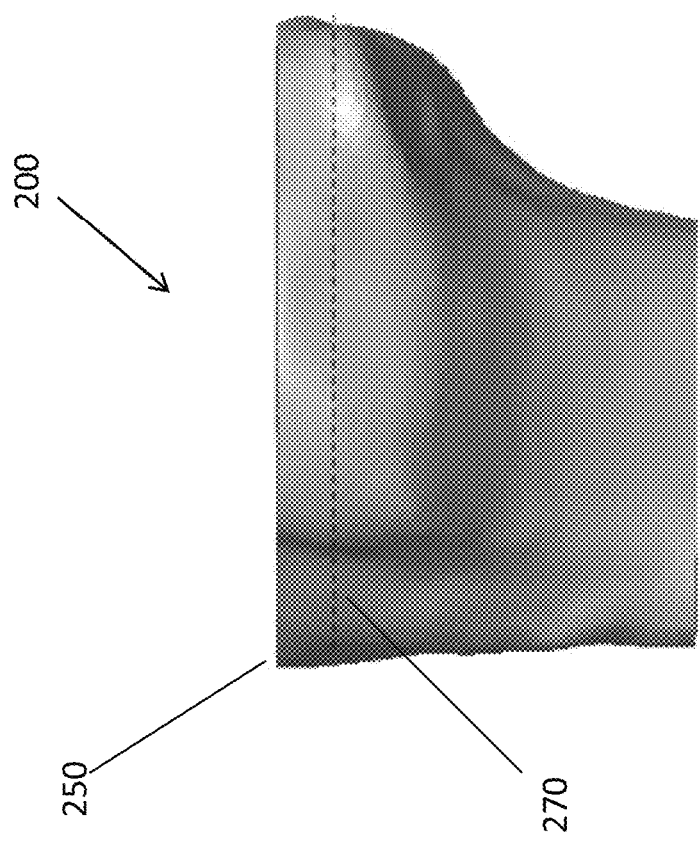
FIG. 4B-C are side and perspective views of the proximal tibia of FIG. 4A after a preliminary bone resection has been performed according to a preliminary resection profile.
Figure 4A:
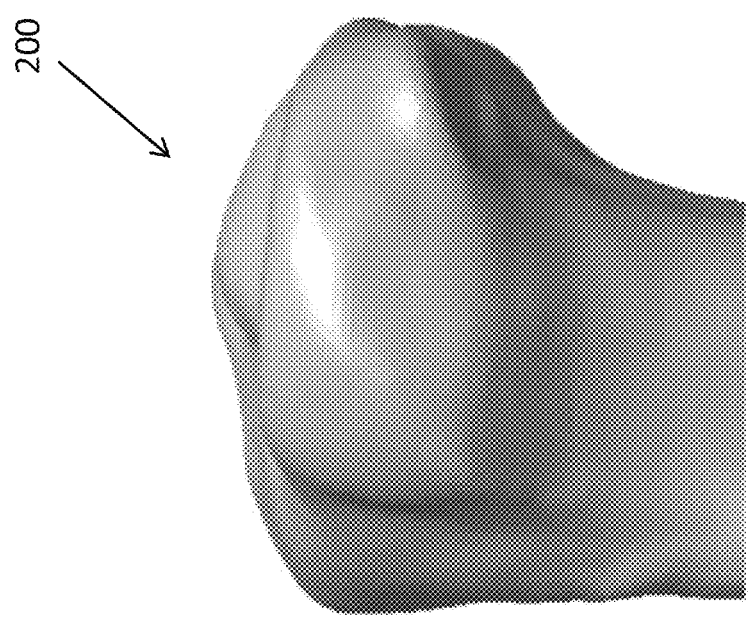
FIG. 4A is a side view of one embodiment of a non-resected proximal tibia.
Figure 4D:
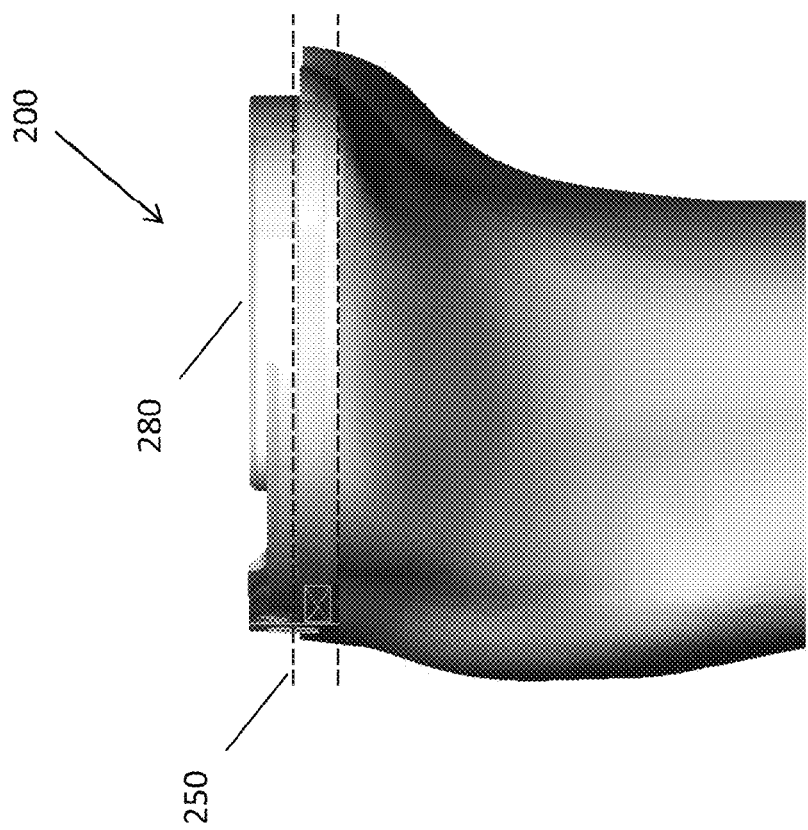
FIG. 4D is a side view of the proximal tibia of FIG. 4A after the preliminary bone resection along with a line indicating the final projected cut plan, including a final planned tibial implant position superimposed on the proximal tibia.
Figure 4C:
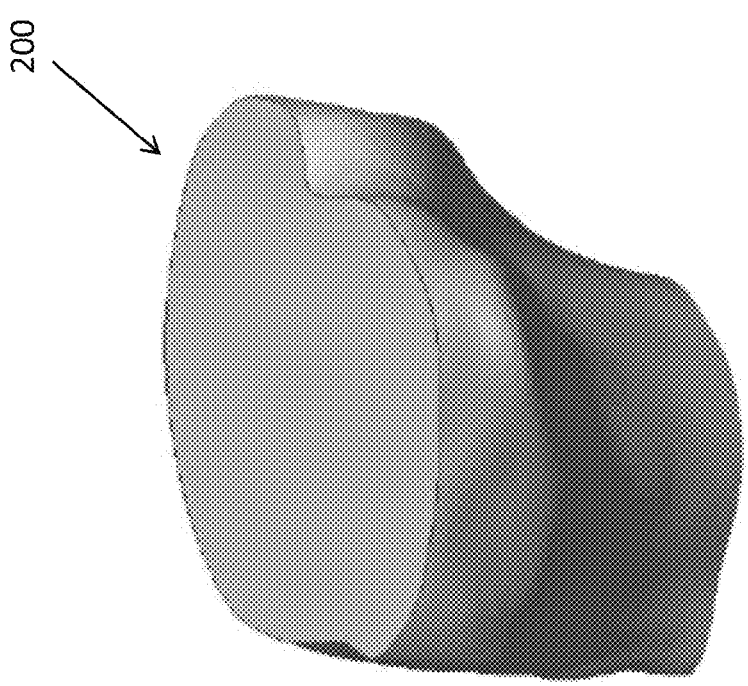

A non-resected proximal tibia 200 is illustrated in FIG. 4A prior to performing any bone preparation. Similar to the procedure described above for the distal femur 100, the proximal tibia 200 may be preliminarily resected in a first step according to a preliminary resection profile 250. The preliminary resection profile may be shallower than the final planned cut 270. The preliminary bone resection is mostly or completely flat or planar, as best illustrated in FIG. 4C. FIG. 4D illustrates the proximal tibia 200 after the preliminary bone resection has been made according to the preliminary resection profile 250. Superimposed on FIG. 4D are the final planned cut 270 and a tibial implant 280 positioned on the proximal tibia 200 in a final position. It should be noted that a preliminary bone resection need not be performed on the proximal tibia 200 in all cases, and in some embodiments the proximal tibia may be finished completely according to a final plan in one step without first performing a preliminary bone resection that allows for further adjustments.

Figure 5:
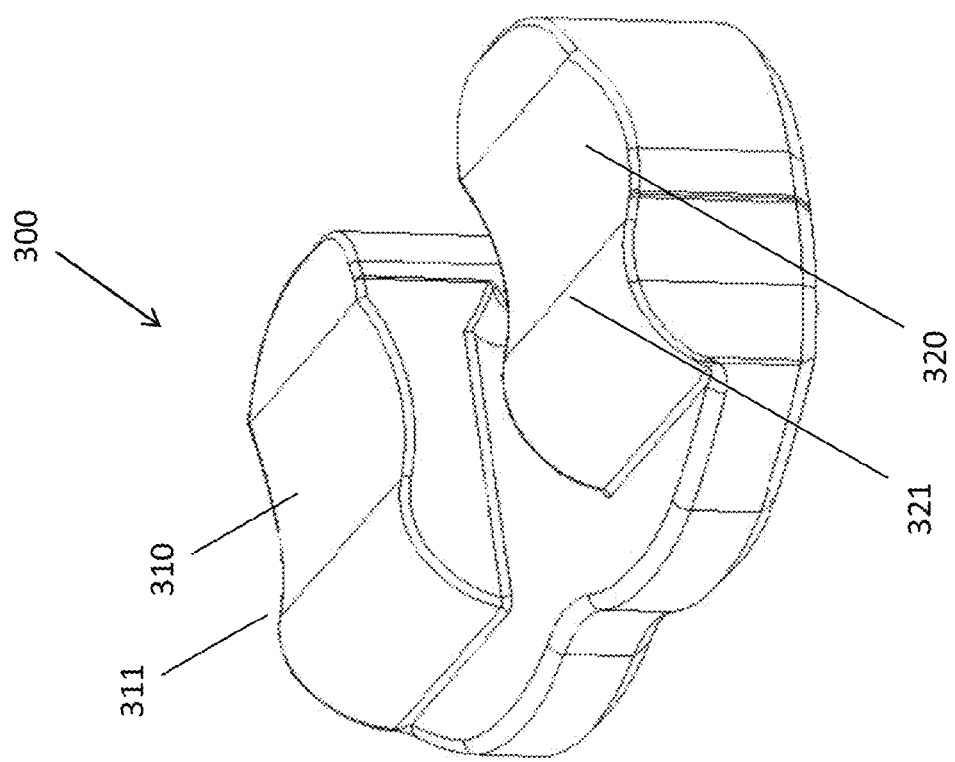
FIG. 5 is a perspective view of one embodiment of a monolithic tibial trial.

FIG. 5 illustrates one embodiment of a tibial trial insert 300 for trialing after the preliminary bone resection is performed according to the preliminary resection profiles 150, 250 in the distal femur 100 and the proximal tibia 200, respectively. The tibial trial insert 300 may include a first groove or sulcus 310 and a second groove or sulcus 320. The grooves may take the form of dished plateaus that correlate with the articular dishes of the tibial implant plateau. The first and second grooves 310, 320 may be sized and positioned to articulate with the articulating surfaces 152 of the first and second condyles 110, 115 after the preliminary bone resection has been performed on the distal femur 100. In the particular embodiment illustrated, the tibial trial insert 300 is monolithic. That is, the tibial trial insert 300 is formed from a single piece of material.

Figure 6A:
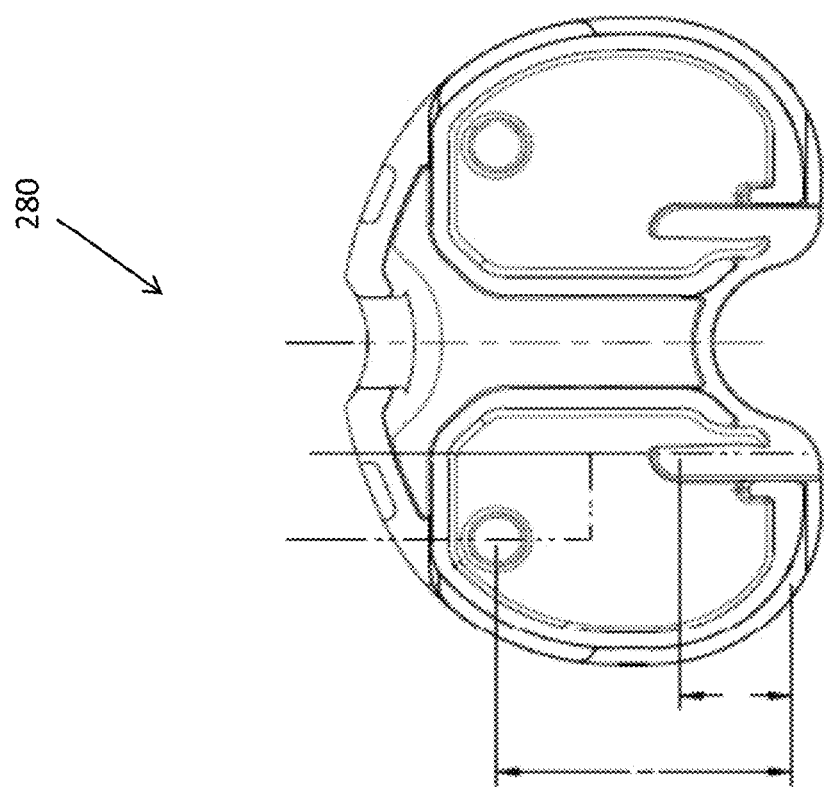
FIGS. 6A-C are multiple views of one embodiment of a tibial implant.
Figure 6C:
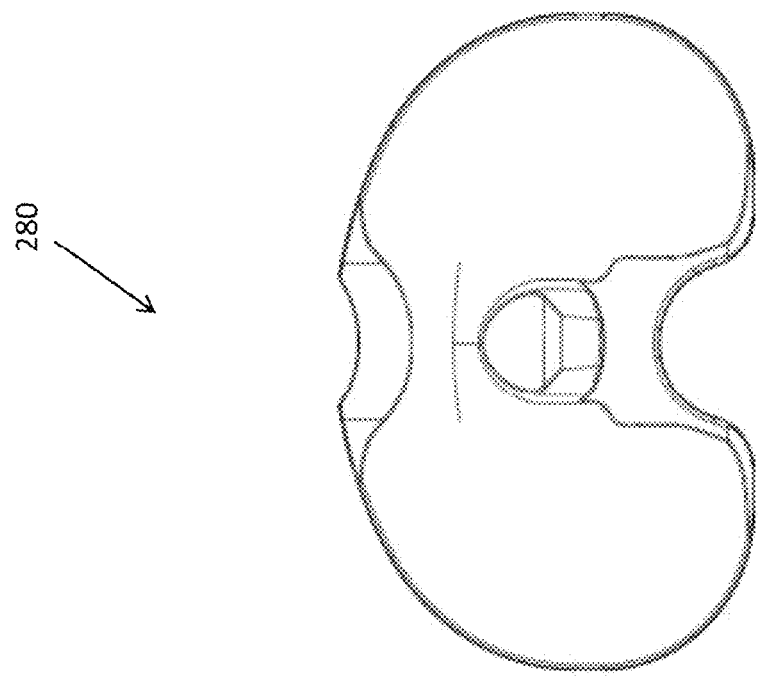
Figure 6B:
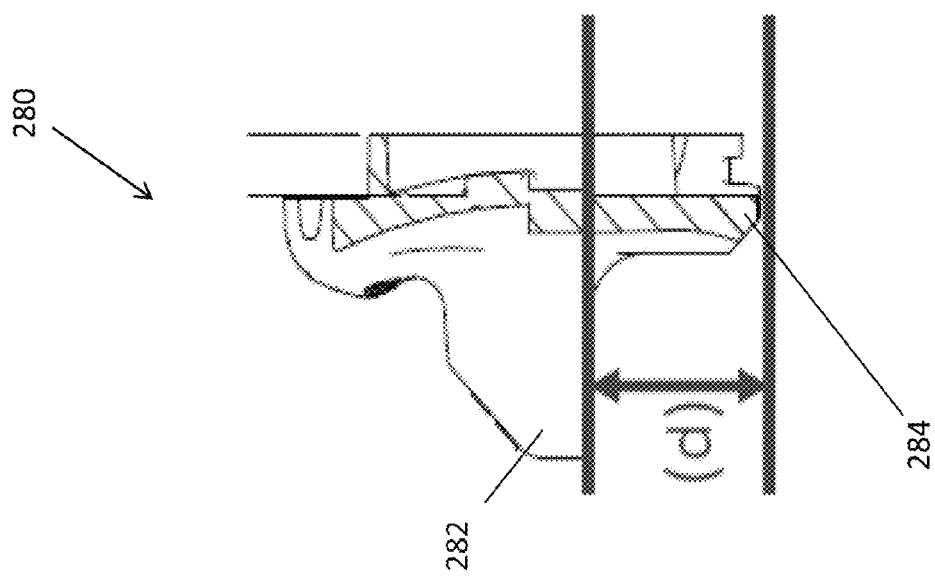

The particular position of the grooves 310, 320 of tibial trial insert 300 may depend upon the particular tibial implant 280 intended for use. FIGS. 6A-C illustrate top, side, and bottom views of an exemplary tibial implant 280, respectively, to be implanted onto the proximal tibia 200 after the final tibial resection is performed (which is performed after trialing with a tibial trial insert 300). As best illustrated in FIG. 6B, the distance d between the anterior portion of post 282 and the anterior portion of tibial implant 280 may be related to the position of the grooves 310, 320 of the tibial trial insert 300. For example, the anterior portions 311, 321 of the respective grooves 310, 320 when inserted on the proximal tibia 200 during trial may align with the anterior portion of post 282 when the tibial implant 280 is implanted on the proximal tibia 200. In other words, the grooves 310, 320 of the tibial trial insert 300 should be positioned with respect to the geometry of the final tibial implant 280 such that articulation between the distal femur 100 (after the preliminary bone resection) and the tibial trial insert throughout the range of motion corresponds to the articulation between the femoral implant 180 and the tibial implant according to the final design plan.

Figure 7B:
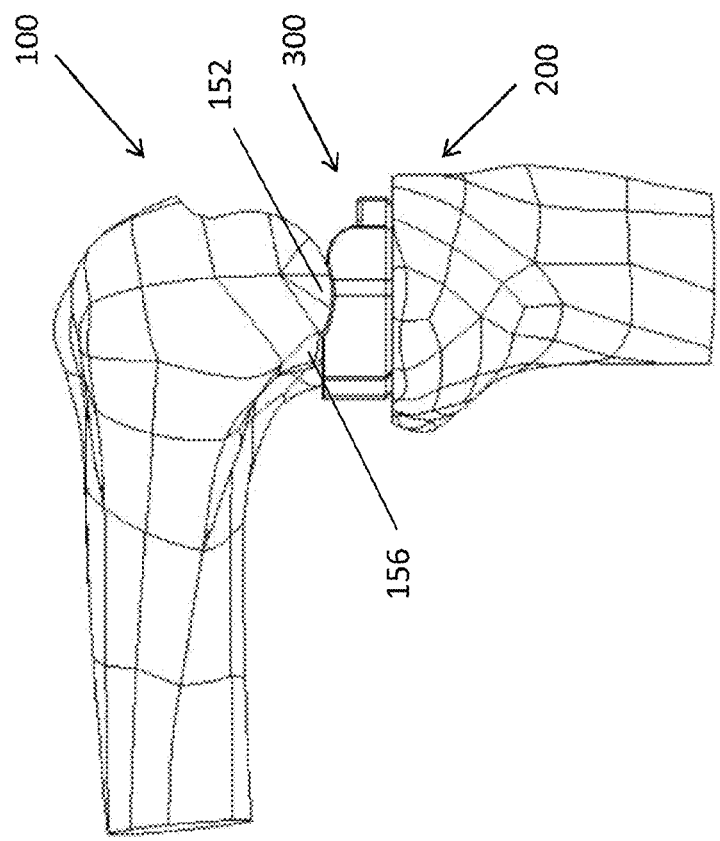
FIGS. 7A-B are perspective views of a knee joint moving from extension to flexion using the tibial trial of FIG. 5.
Figure 7A:
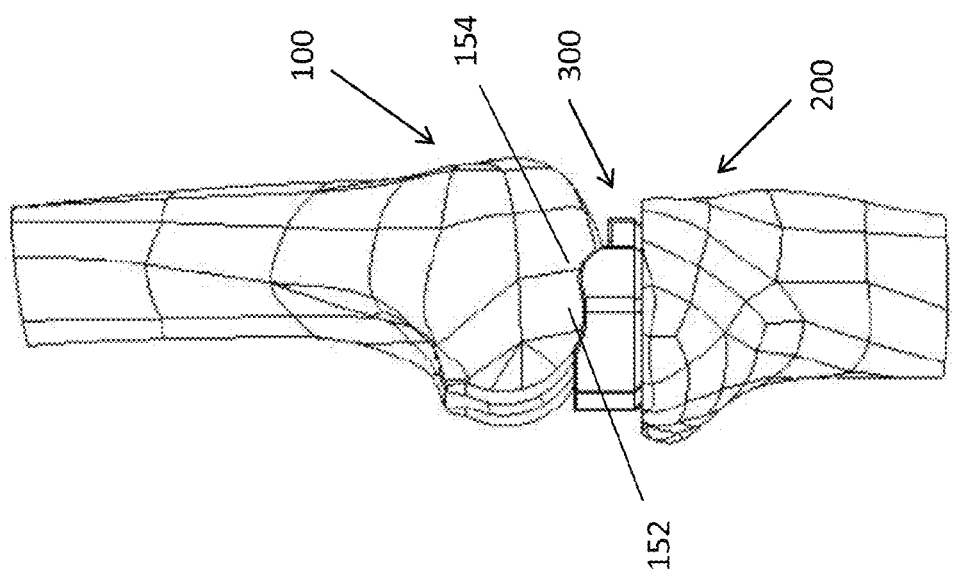

After the preliminary resections of the distal femur 100 and proximal tibia 200 are performed, the surgeon may perform trialing. FIG. 7A illustrates the distal femur 100 and proximal tibia 200 in extension with tibial trial insert 300 positioned on the proximal tibia. In this position, the rounded articulating portions 152 of each condyle 110, 115 of the distal femur 100 sit within the respective grooves 320, 310 of the tibial trial insert 300. In extension, the anterior stops 154 make contact with an anterior portion of the tibial trial insert 300, setting an approximate limit to how far the knee may be placed into extension. In flexion, as illustrated in FIG. 7B, the posterior stops 156 make contact with a posterior portion of the tibial trial insert 300, setting an approximate limit to how far the knee may be placed into flexion.

The shape of the distal femur 100 following the preliminary bone resection is configured to correspond to the shape of the femoral implant 280, for example by having coaxial flexion axes, and to articulate with the tibial trial insert 300, as described above. This may provide the ability for the surgeon to take the knee through a range of motion to perform trialing without the need of a separate femoral trialing component and, as described above, correlate to the positional alignment of the final design plan of the implants. For example, the knee may be taken through a range of motion from extension, through mid-range flexion and then into deep flexion (for example, in approximately 0, 30, 60, 90 and 120 degrees of flexion) to analyze the kinematics of the joint. In each desired position, the surgeon may determine the size of the gap between each femoral condyle 110, 115 and the proximal tibia 200 to determine whether the gaps are properly balanced. By articulating the proximal tibia 200 with respect to the distal femur 100, the surgeon may determine a second area of bone to remove from the distal femur 100. This second removal of bone may be either a secondary machining for fine tuning, or may be an adjustment to the final femoral cut plan 170.

The decision of whether any change should be made to the final design plan may be based on a number of positional alignment target values. For example, one particular target may be that the gaps in both flexion and extension result in no more than two degrees offset from the neutral, mechanical axis regarding the overall limb alignment, although other target values, including for example one degree or three degrees, may be used. Another goal may be that the flexion gap should be equal to or greater by approximately 3 mm relative to the extension gap, although greater or smaller targets may be used. A further target may be that the flexion gap produces a force measurement that is equal or up to approximately 10% greater than the force measurement produced by the extension gap, although other target percentages may be appropriate. The above gap balancing targets are merely illustrative and other targets may be implemented as desired by the surgeon. If the values determined during this kinematic analysis are not acceptable, the surgeon may release soft tissue to attempt to reach acceptable values. Alternatively or in addition to soft tissue release, the surgeon may adjust the rotational and/or translational degrees of freedom of the implant position in the design model and/or perform additional bone removal based on the new design model. After the surgeon performs fine tuning and/or minor adjustments, if necessary, he may repeat the kinematic analysis to determine if the new values are acceptable. Either or both of these steps may be repeated in an iterative fashion until the surgeon is satisfied with the kinematic analysis at this intermediate stage.

Figure 9B:
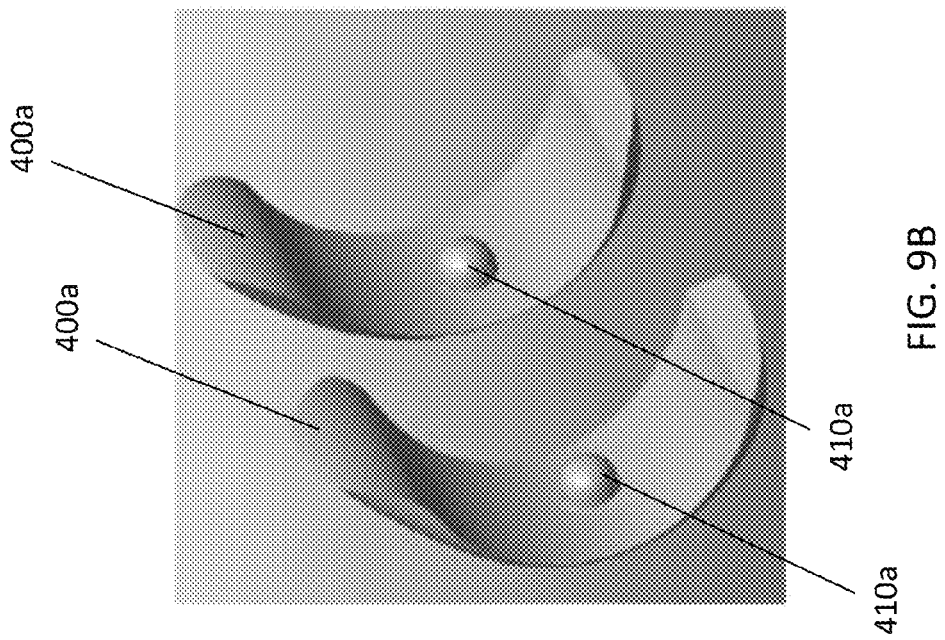
FIGS. 9A-B are perspective views of an alternate embodiment of femoral shims.
Figure 9A:
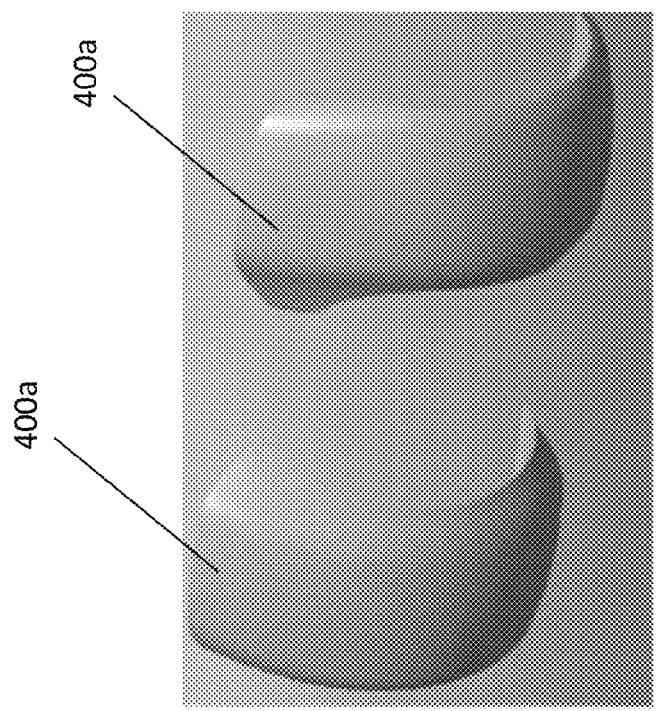
Figure 9D:
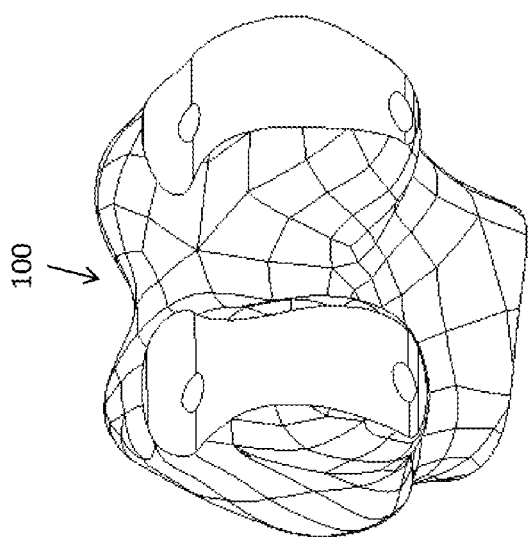
FIG. 9D is a perspective view of a prepared femur corresponding to the femoral shims of FIG. 9C.
Figure 9C:
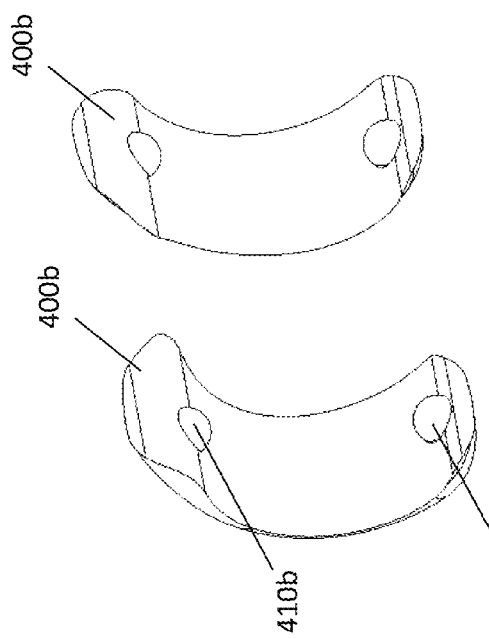
FIG. 9C is a perspective view of another embodiment of femoral shims.
Figure 9E:
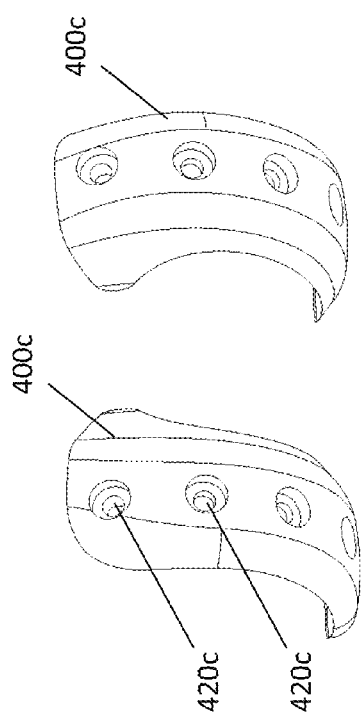
FIG. 9E is a perspective view of a further embodiment of femoral shims.

FIGS. 8A-B illustrate shims 400 that may be attached to the distal femur 100 after the preliminary femoral bone resection is performed according to the preliminary resection profile 150. The illustrated shims 400 may be particularly useful if the preliminary resection profile is a curved resection profile, although other shims, described below, may be particularly useful if the preliminary resection profile is a planar resection profile. The shims 400 may be useful, for example, to provide the surgeon the ability to trial the femur using trial inserts not specifically designed for use with the curved bone profile. In one embodiment, as illustrated in FIGS. 8C-D, the shims 400 are designed in relation to the femoral implant 180 and the curved resection profile. FIG. 8C illustrates the femoral implant 180, and FIG. 8D includes the curved resection profile superimposed on the femoral implant 180. The shims 400 each have an articulation surface configured to match the shape of the femoral implant 180, minus the curved resection profile. A first alternate pair of shims 400a is illustrated in FIGS. 9A-B. Shims 400a are substantially identical to shims 400 with the exception that shims 400a include a peg 410a on the bone contacting surface to facilitate fixation to the distal femur 100. A second alternate pair of shims 400b is illustrated in FIG. 9C. Shims 400b are substantially identical to shims 400a with the exception that each shim 400b includes a first peg 410b near a first end and a second peg 410b near a second end. As illustrated in FIG. 9D, the distal femur 100 may be machined with corresponding holes to mate with first and second pegs 410b. A third alternate pair of shims 400c is illustrated in FIG. 4E. Shims 400c are substantially similar to shims 400b, but do not include pegs 410b and rather include a plurality of holes 420c. Fasteners, such as bone screws, may be used to attach the shims 400c to the distal femur 100 through the holes 420c.

Figure 9G:
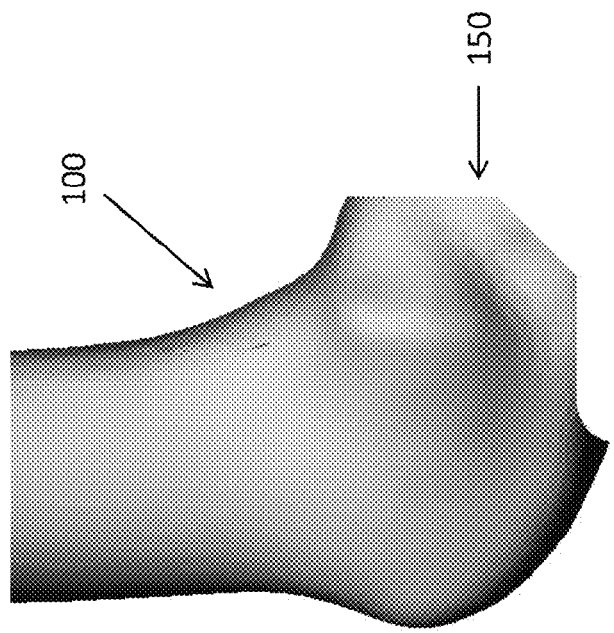
FIG. 9G is a side view of the distal femur of FIG. 9F after a preliminary bone resection has been performed according to the planar resection profile.
Figure 9F:
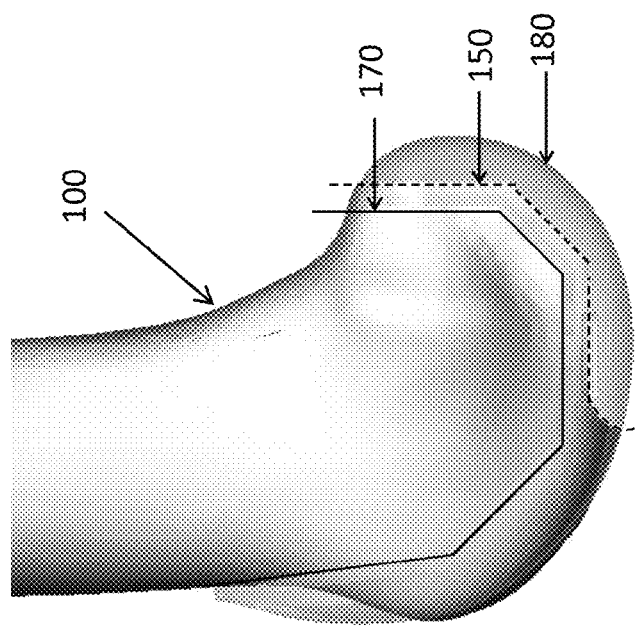
FIG. 9F is a side view of a distal femur including broken lines indicating a preliminary planar resection profile along with a plurality of solid planar lines indicating a final projected cut plan, including a final planned femoral implant position superimposed on the distal femur.
Figure 9I:
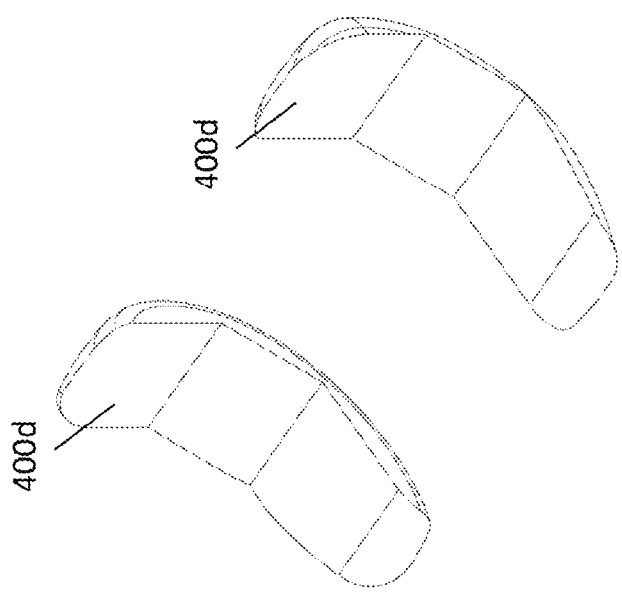
FIGS. 9H-J are perspective and side views of alternate femoral shims configured for use with the distal femur of FIG. 9G.
Figure 9H:
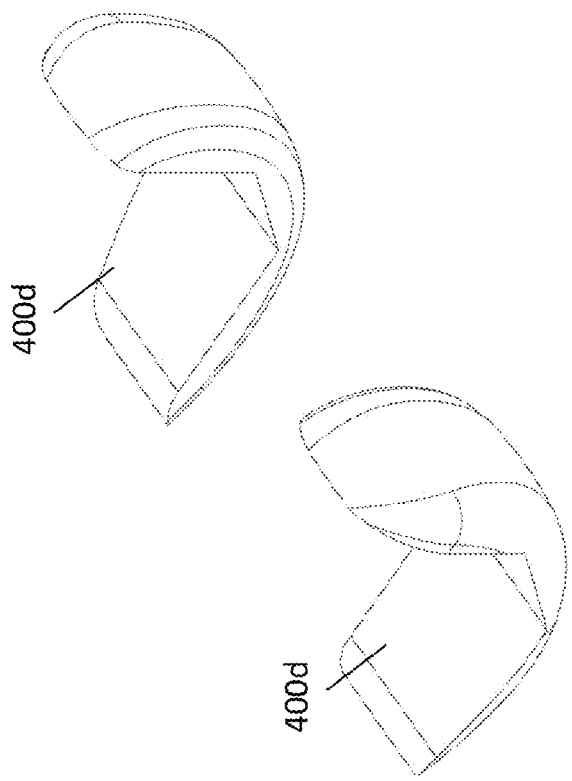
Figure 9K:
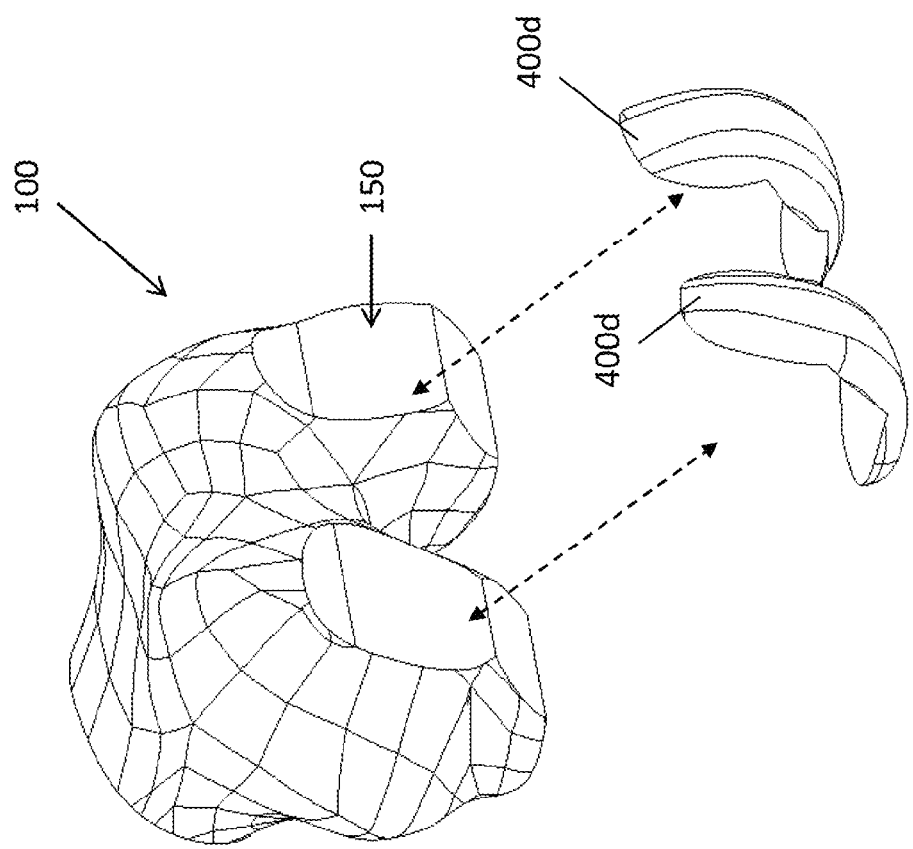
FIG. 9K is a perspective view of the distal femur of FIG. 9G illustrated with respect to the position of femoral shims of FIGS. 9H-J.
Figure 9J:
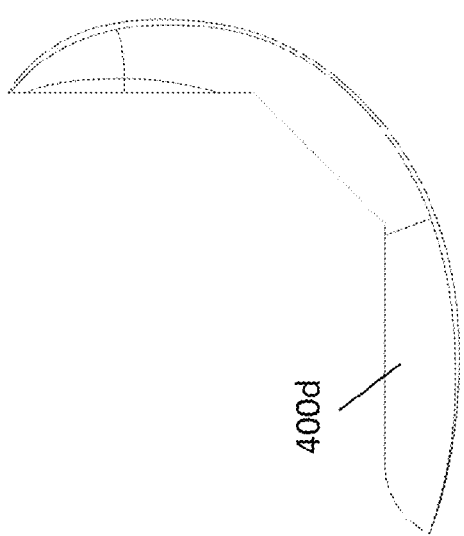

It should further be noted that the interior of shims need not be rounded. For example, as illustrated in FIGS. 9F-G and as described above, the distal femur 100 may be prepared with a preliminary bone resection according to a preliminary resection profile 150 that consists mostly of planar cuts. As can be seen, particularly in FIG. 9F, the planar resection profile is offset a few millimeters from the final projected cut plan 170, much in the same way as described above in relation to the curved resection profile. As illustrated in FIGS. 9H-J, shims 400d with planar inner surfaces that correspond to the planar resection profile may be mated to the distal femur 100 in any of the previously described ways. Shims 400d may be identical to any of the previously described shims, with the exception that the inner surfaces are planar and correspond to the planar resection profile illustrated in FIGS. 9F-G. Although the distal femur 100 cannot be used directly for intraoperative trialing in this case because of the preliminary bone resection according to the planar resection profile, shims 400d provide the articulating surface which, along with the distal femur, correlates to the distal-posterior condyles of the final femoral implant to facilitate intraoperative trialing. This configuration may be especially useful when the intended femoral implant is one without a "single radius" configuration.

Figure 10:
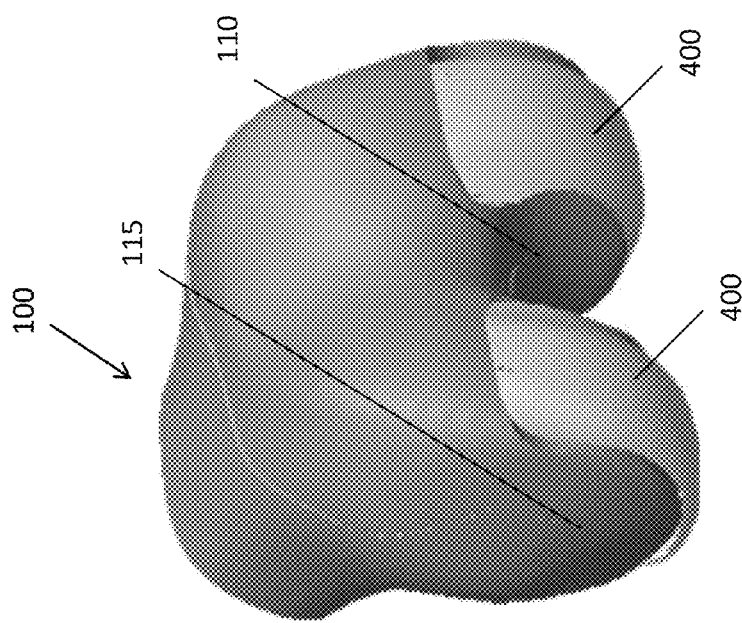
FIG. 10 is a perspective view of a distal femur with femoral shims attached thereto.

The distal femur 100 is illustrated in FIG. 10 after the preliminary femoral bone resection has been performed according to the curved resection profile. However, shims 400 have been placed on the femoral condyles 110, 115. The shims 400 provide an outer articulating surface that matches the shape of the femoral implant 180. In addition, the design of the shims 400 provides or maintains a flexion axis that is coaxial with the flexion axis of the implant according to the final design plan, such that trialing may be performed after the preliminary femoral bone resection has been completed.

Figure 11A:
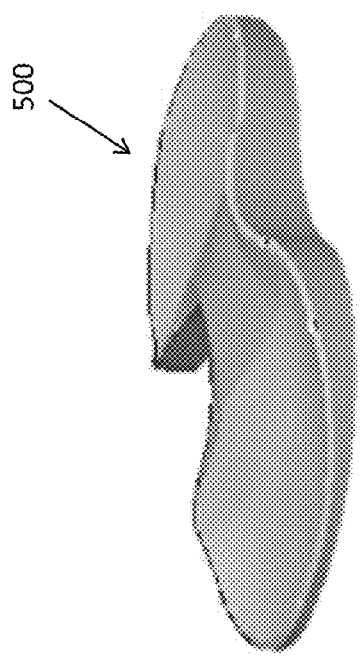
FIG. 11A is a perspective view of one embodiment of a tibial insert.

One embodiment of a tibial trial insert 500 that may be used with the distal femur 100 and shims 400 is illustrated in FIG. 11A. Tibial trial insert 500 is a constant volume device that provides variable pressure, and may include load sensing capabilities to provide a variety of measurements to the surgeon during trialing. A trial including load sensing elements in the medial and lateral compartments may further include a receiver and/or a transmitter for receiving and/or transmitting information regarding sensed load to a computer, which in turn may display the information on a display, such as a graphic user interface ("GUI"), to inform the surgeon of loads being applied to the insert trial. The information may be transmitted wirelessly or the insert may be hardwired to a computer. Power may be supplied by the wire or otherwise, including, for example, battery power.

The shims 400 are not necessary for trialing in all cases, for example if trialing were performed with a trial insert designed specifically to be congruent to a curved resection profile, such as tibial trial insert 300 described with reference to FIG. 5. A constant volume trial may provide the surgeon with rectangular joint spaces/gaps during trialing assessment. With this space, the surgeon can assess the effect that the surrounding soft tissue, including ligaments, tendons, etc., has on the overall joint space and make necessary adjustments, such as performing ligament releases.

Figure 11B:
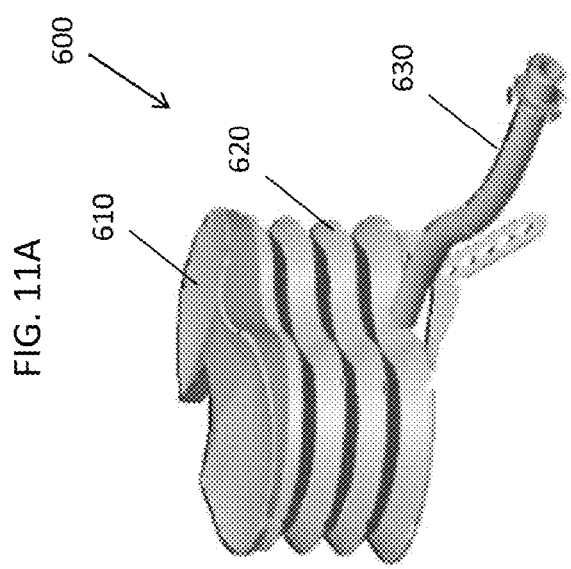
FIG. 11B is a perspective view of one embodiment of an expandable and contractable tibial insert.
Figure 11C:
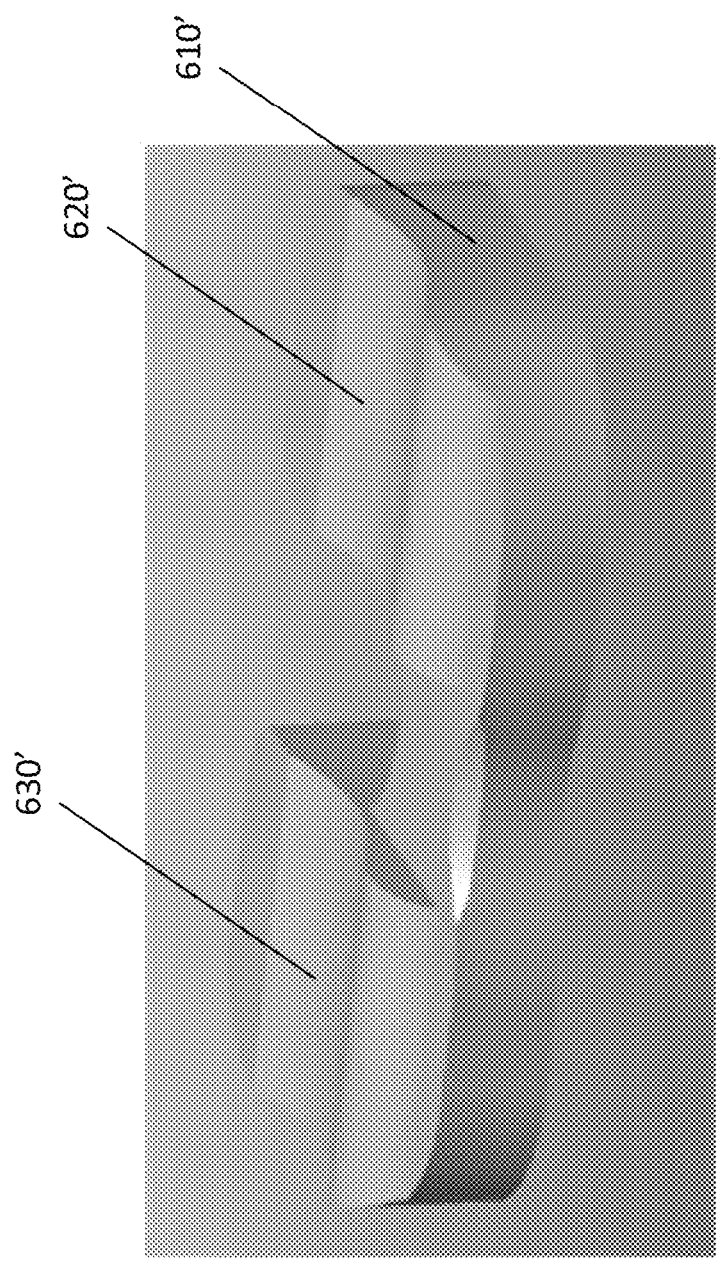
FIG. 11C is a perspective view of one embodiment of a modified surface of the tibial insert of FIG. 11B.
Figure 11D:
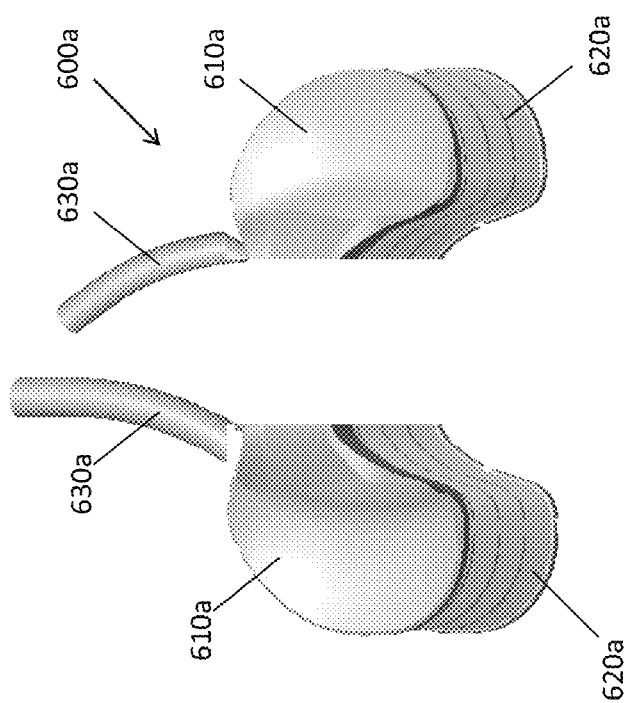
FIG. 11D is a top perspective view of an alternate embodiment of expandable and contractable medial and lateral tibial inserts.
Figure 11E:
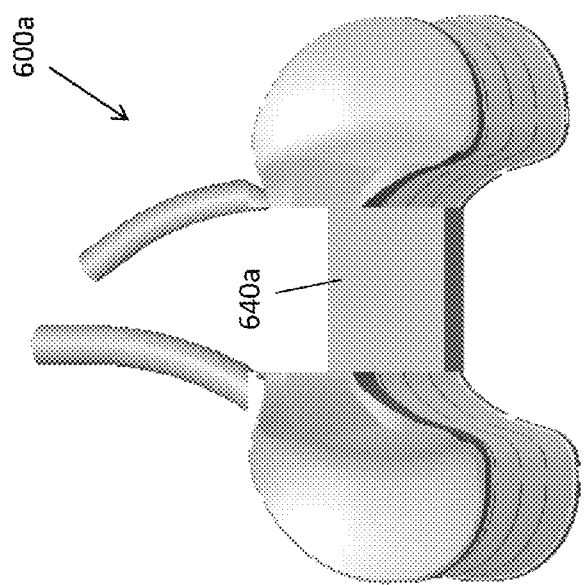
FIG. 11E is a top perspective view of the tibial insert of FIG. 11D with optional connecting hardware illustrated.

Alternately, trialing may be performed using a constant pressure, variable volume trial insert 600 if desired. With a constant pressure trial, as opposed to a constant volume trial, the joint may tend to find a position of equilibrium that results in a malposition or imbalance (i.e. varus or valgus) during trial assessment. In this mode, the surgeon addresses the variable volume by, for example, performing ligament releases iteratively until the malposition or imbalance is corrected. For example, FIG. 11B illustrates a tibial trial insert 600 that includes an insert surface 610, which may be similar or identical to the tibial trial insert 500. The insert surface 610 is connected to a component with a volume that may expand or contract, for example bellows 620. Bellows 620 may be connected to a fluid source through the lumen of a tube 630. The fluid source may, for example, be capable of pumping air or saline into the bellows 620 through the tube 630 to provide for constant pressure and variable volume during trialing. The insert surface 610 may also be modified to have the surface 610', illustrated in FIG. 11C. Insert surface 610' is substantially the same as the surface of tibial trial insert 300 described above with reference to FIG. 5. Essentially, insert surface 610' includes a sulcus or groove 620', 630' for each femoral condyle 110, 115 to provide for articulation with the distal femur 100 without the need for shims 400. Another embodiment of a variable volume insert 600a is illustrated in FIG. 11D. This insert 600a is similar to insert 600, but includes two separate surfaces 610a and bellows 620a, each attached to a tube 630a. This embodiment provides for independent filling of the portions of insert 600a corresponding to the separate medial and lateral femoral condyles 110, 115. As illustrated in FIG. 11E, a solid member 640a may be used to physically (but not fluidly) connect the separate bellows 620a for ease of handling, insertion, etc.

Figure 12A:
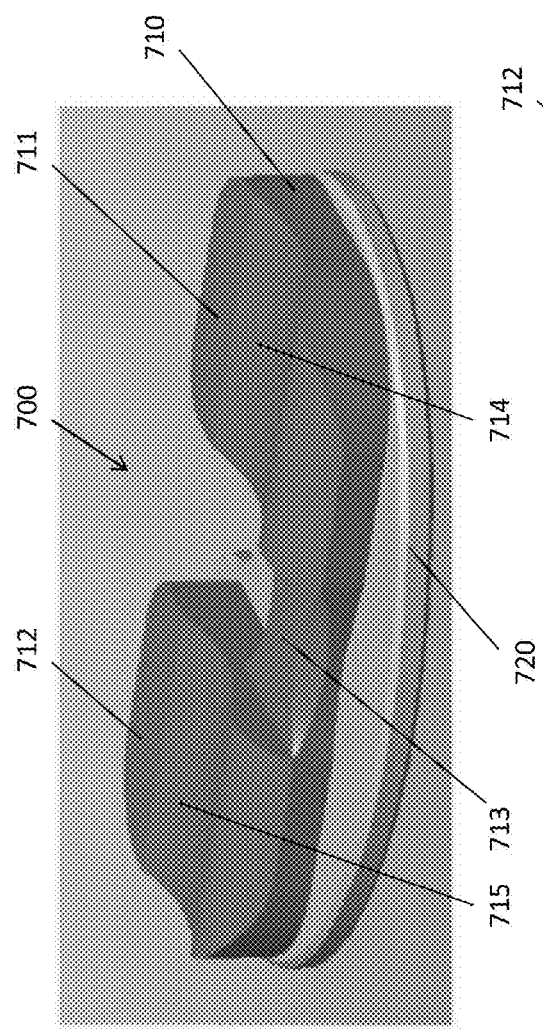
FIGS. 12A-B are perspective and front views of one embodiment of a modular tibial trial according to an aspect of the invention.
Figure 12B:
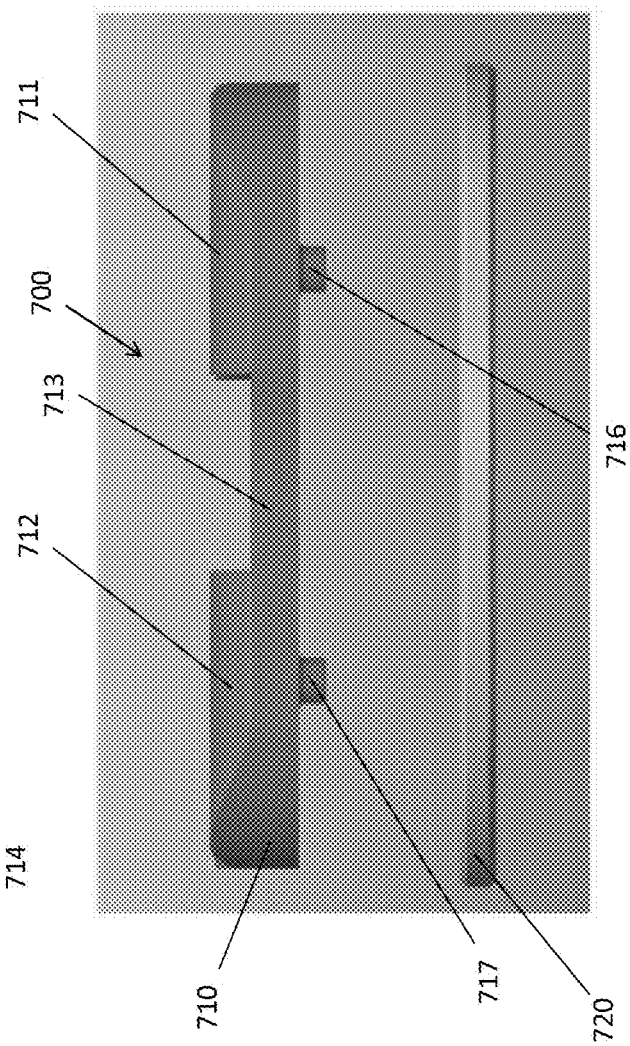

A number of variations may be made to the tibial trial inserts for use with the native bone (with or without shims 400) of the distal femur 100 after the preliminary bone resection has been performed according to the preliminary resection profile 150. For example, a modular tibial trial 700 is illustrated in FIGS. 12A-B. The modular tibial trial 700 may include an insert 710 and a shim 720. The insert 710 may have a number of features similar to other inserts described herein. For example, the insert 710 may include a first condylar portion 711 and a second condylar portion 712 connected by a bridge 713 at anterior ends of the first and second condylar portions. A proximal surface of the first condylar portion 711 may include a sulcus or groove 714 and a proximal surface of the second condylar portion 712 may also include a sulcus or groove 715. As described above, each groove 714, 715 may be configured to correspond with the dished plateaus of the tibial implant and provide articulation with the machined surface of the distal femur 100 after it is resected according to the preliminary resection profile 150. The distal surface of the insert 710 may include pegs 716, 717 configured to be inserted in corresponding holes in the shim 720 (holes not visible in FIGS. 12A-B).

Figure 13A:
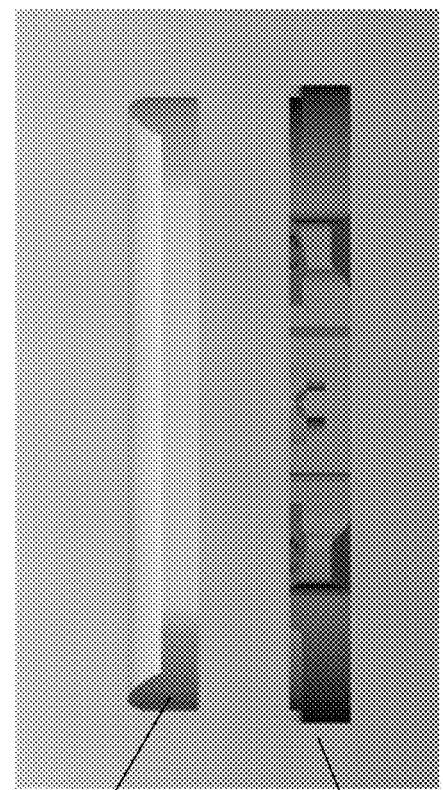
FIGS. 13A-B are perspective and front views of another embodiment of a modular tibial trial insert and template according to an aspect of the invention.
Figure 13B:
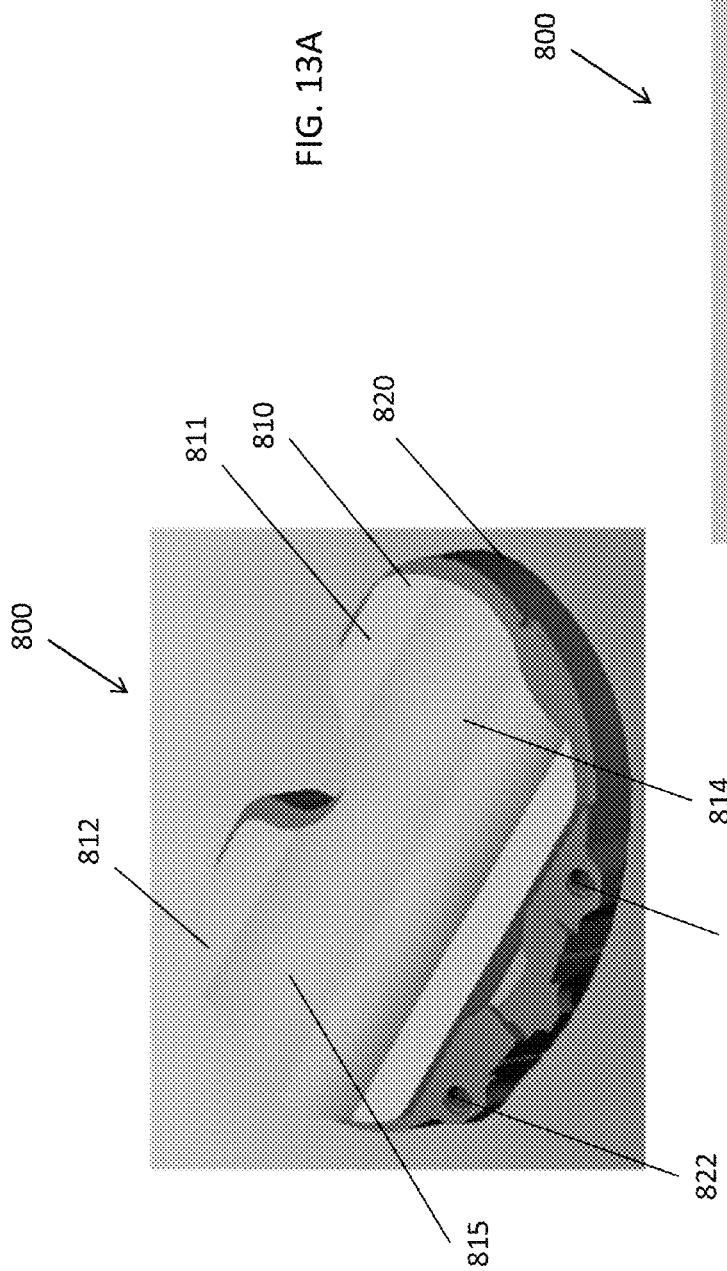

Another embodiment of a tibial trial 800 is illustrated in FIGS. 13A-B. Similar to trial 700, trial 800 is modular and may be used with the native bone of the distal femur 100 (with or without shims 400) after the preliminary resection has been performed according to the preliminary resection profile 150. Tibial trial 800 may include an insert 810 and a template 820. The insert 810 may have a number of features similar to other inserts described herein. For example, insert 810 may include a first condylar portion 811 and a second condylar portion 812. A proximal surface of the first condylar portion 811 may include a sulcus or groove 814 and a proximal surface of the second condylar portion 812 may also include a sulcus or groove 815. Although the grooves 814, 815 are described as being included on the proximal surfaces of the first and second condylar portions 811, 812, it should be apparent that the grooves may take the form of a continuous groove across the proximal surface of the insert 810. As described above, each groove 814, 815 may be configured to correspond with the dished plateaus of the tibial implant and provide articulation with the machined surface of the distal femur 100 after it is resected according to the preliminary resection profile 150. The distal surface of the insert 810 may be configured to be inserted into the template 820 by, for example, press-fitting, snap fitting, tongue-in-groove fitting, etc.

The template 820 may include a plurality of fixation holes 822 at an anterior end of the template. The template 820 may be fixed to the proximal tibia 200 with fixation pins that extend through fixation holes 822 and into the bone. The fixation holes 822 may be angled, allowing a surgeon to insert fixation pins through the fixation holes 822 with less clearance required than if the fixation holes were not angled. Requiring less clearance may be beneficial, for example, because it may allow a surgeon to fix the template 820 to the bone without repositioning, or only minimally repositioning, the distal femur 100, proximal tibia 200, or other portions of the patient's anatomy.

Figure 14A:
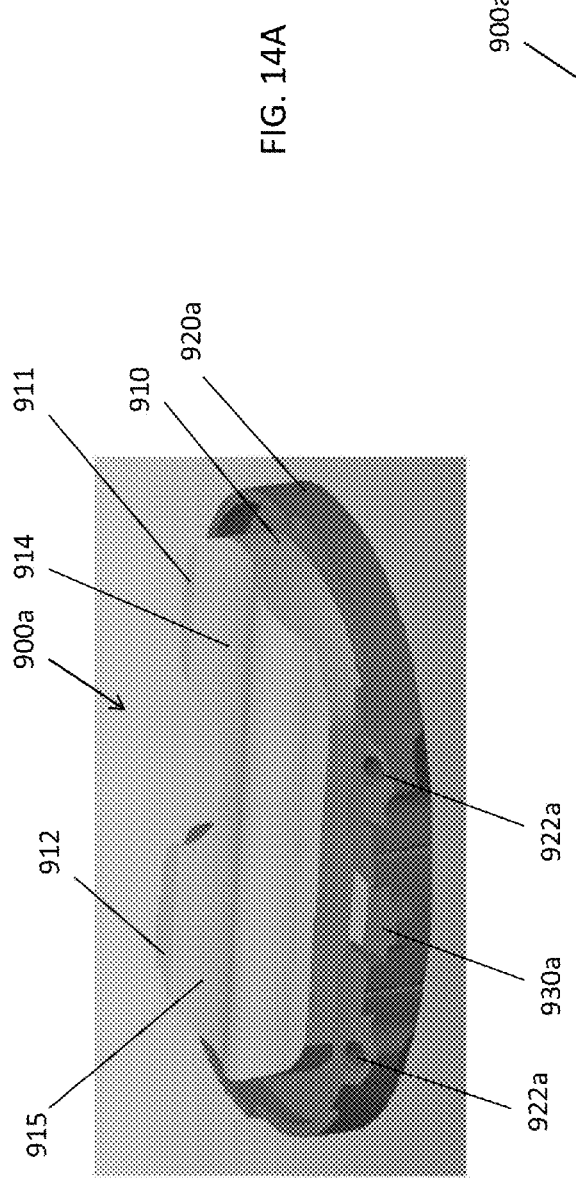
FIGS. 14A-B are perspective and front views of another embodiment of a modular tibial trial insert and template according to another aspect of the invention.
Figure 14B:
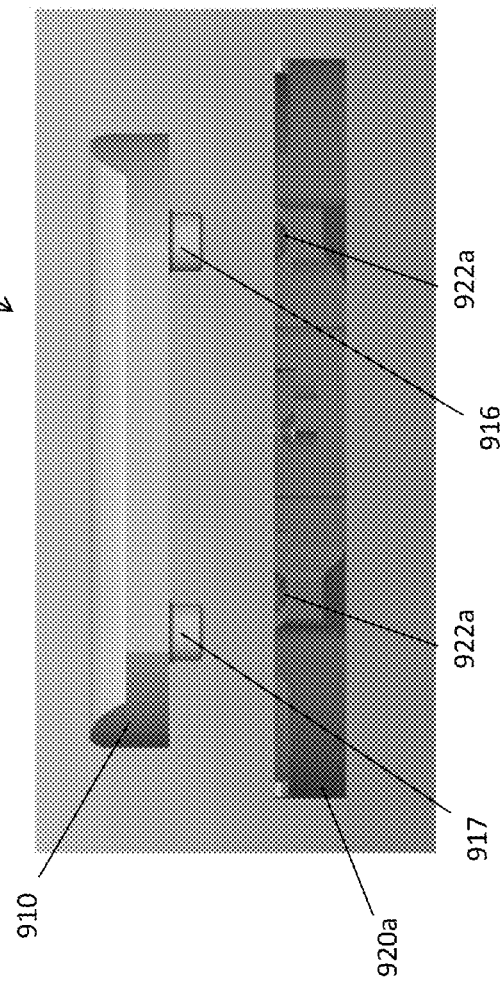
Figure 14C:
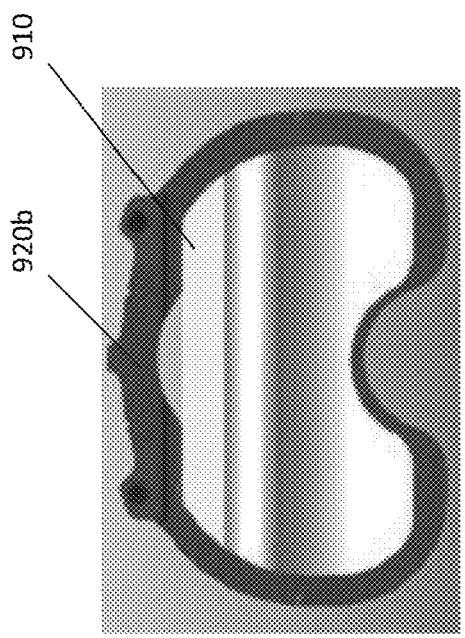
FIGS. 14C-F are top views of the various sized templates housing the insert of FIGS. 14A-B therein.
Figure 14D:
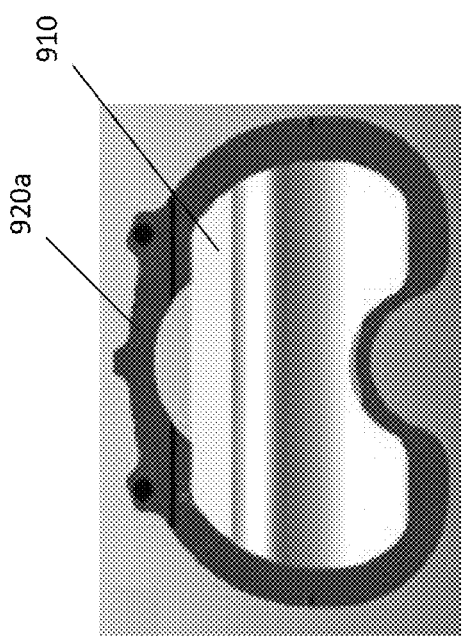
Figure 14E:
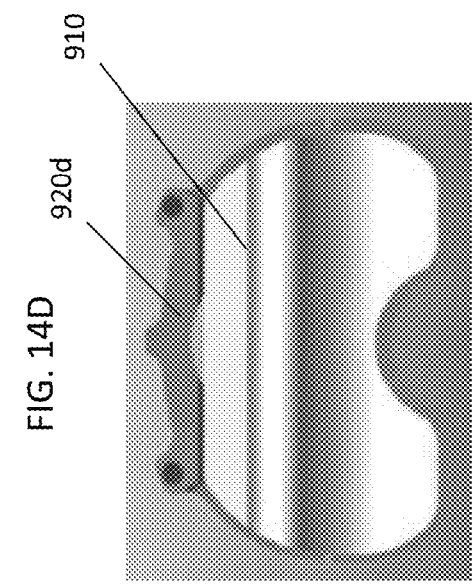
Figure 14F:
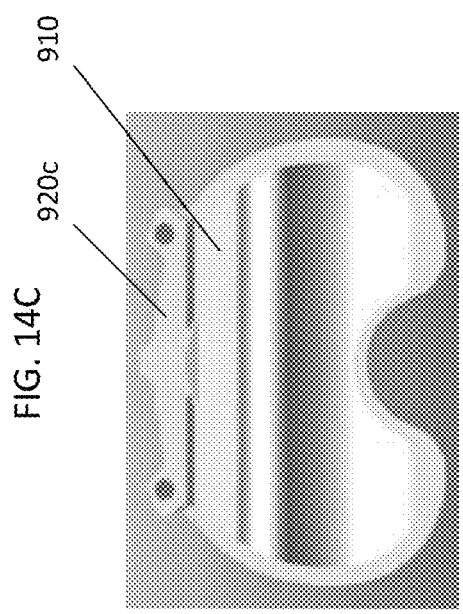

A further embodiment of a tibial trial 900a is illustrated in FIGS. 14A-B. Similar to trial 800, trial 900a is modular and may be used with the native bone of the distal femur 100 (with or without shims 400) after the preliminary resection has been performed according to the preliminary resection profile 150. Tibial trial 900a may include an insert 910 and a template 920a. The insert 910 may have a number of features similar to other inserts described herein. For example, insert 910 may include a first condylar portion 911 and a second condylar portion 912. A proximal surface of the first condylar portion 911 may include a sulcus or groove 914 and a proximal surface of the second condylar portion 912 may also include a sulcus or groove 915. Although the grooves 914, 915 are described as being included on the proximal surfaces of the first and second condylar portions 911, 912, it should be apparent that the grooves may take the form of a continuous groove across the proximal surface of the insert 910. As described above, each groove 914, 915 may be configured to correspond with the dished plateaus of the tibial implant and provide articulation with the machined surface of the distal femur 100 after it is resected according to the preliminary resection profile 150. The distal surface of the insert 910a may include pegs 916, 917 configured to be inserted in corresponding holes in the template 920a (holes not visible in FIGS. 14A-B).

The template 920a may include a plurality of fixation holes 922a at an anterior end of the template. The template 920a may be fixed to the proximal tibia 200 with fixation pins that extend through fixation holes 922a and into the bone. The fixation holes 922a may be angled, allowing a surgeon to insert fixation pins through the fixation holes 922a with less clearance required than if the fixation holes were not angled. The template 920a may also include a groove 930a on an anterior portion thereof. The groove 930a may provide clearance between the template 930a and the insert 910 such that a surgeon may relatively easily grasp and remove insert 910 from template 920a if desired.

The insert 910 and template 920a may be part of a set or a kit of inserts and templates. For example, one exemplary kit may include a small insert 910 and four increasingly sized templates 920a-d, with template 920a being the smallest and 920d being the largest, as illustrated in FIGS. 14C-F. The kit may also include a large insert and another four sized templates (not illustrated). Even further, each of the small and large inserts may be provided with a number of different thicknesses. In one embodiment, the kit contains five thicknesses for each of the small land large inserts, for a total of ten inserts and eight templates. As with other modulate trials described herein, the templates 920a-d may each be able to mate with inserts other than insert 910 to allow a surgeon the flexibility to use a traditional insert with one of the templates 920a-d in conjunction with the distal femur 100 with shims 400 attached.

Figure 15B:
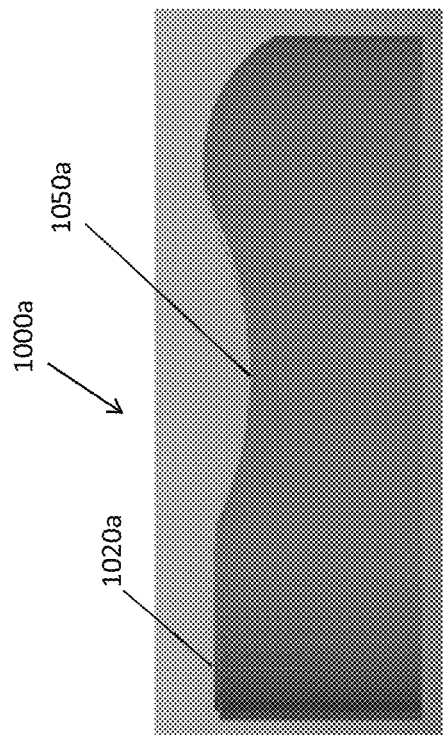
FIGS. 15A-B are perspective and side views of one embodiment of a monolithic tibial insert according to another aspect of the invention.
Figure 15C:
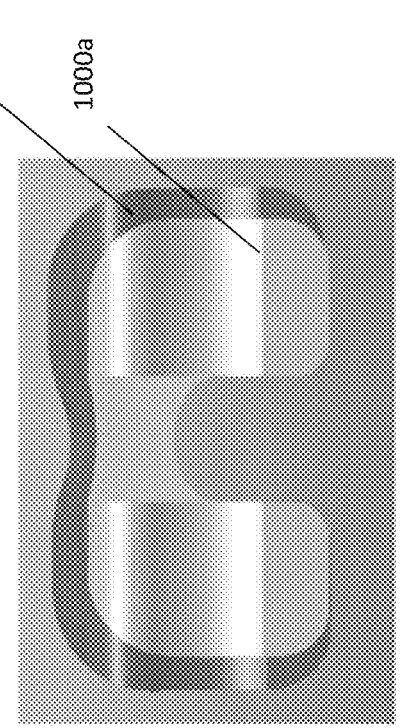
FIG. 15C is a top view of the monolithic tibial insert of FIGS. 15A-B overlaid on a larger monolithic tibial insert.
Figure 15A:
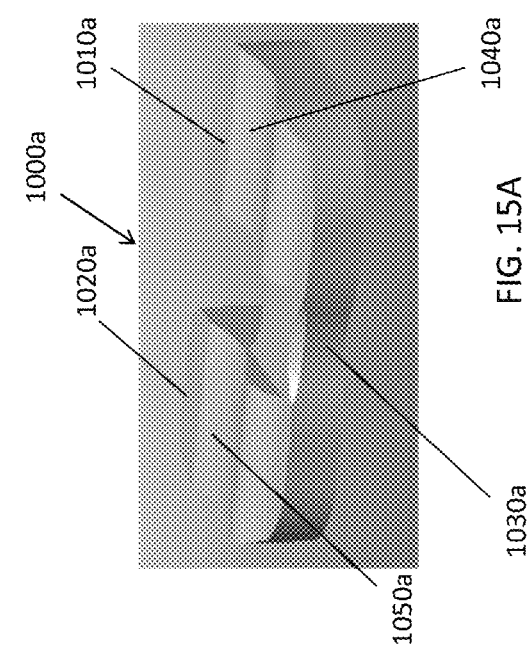

Another monolithic trial insert 1000a is illustrated in FIG. 15A. The trial insert 1000a may be a single piece. The insert 1000a may have a number of features similar to other inserts described herein. For example, the insert 1000a may include a first condylar portion 1010a and a second condylar portion 1020a connected by a bridge 1030a at anterior ends of the first and second condylar portions. A proximal surface of the first condylar portion 1010a may include a sulcus or groove 1040a and a proximal surface of the second condylar portion 1020a may also include a sulcus or groove 1050a. As described above, each groove 1040a, 1050a may be configured to correspond with the dished plateaus of the tibial implant and provide articulation with the machined surface of the distal femur 100 after it is resected according to the preliminary resection profile 150. Trial insert 1000a may be part of a set or a kit of different sized monolithic trial inserts. In one example, a kit of trial inserts may include two groups of four inserts for a total of eight inserts. The four inserts of a first group may each have an identical or nearly identical profile, as illustrated in FIG. 15B, but each have different perimeters. Similarly, the four inserts of a second group may each have an identical or nearly identical profile, the profile of the inserts of the second group being greater than the profile of the inserts of the first group. Again, each insert in the second group may have a different perimeter with respect to one another. FIG. 15C particularly illustrates the difference in perimeter sizes of two inserts 1000a, 1000b of an exemplary kit.

Figure 16B:
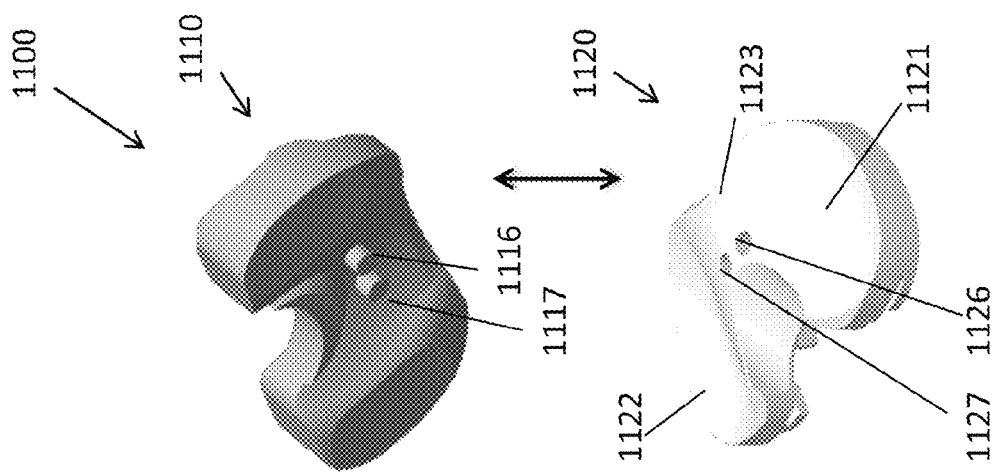
FIGS. 16A-B illustrate perspective views of a dual-use tibial trial according to another aspect of the invention.
Figure 16A:
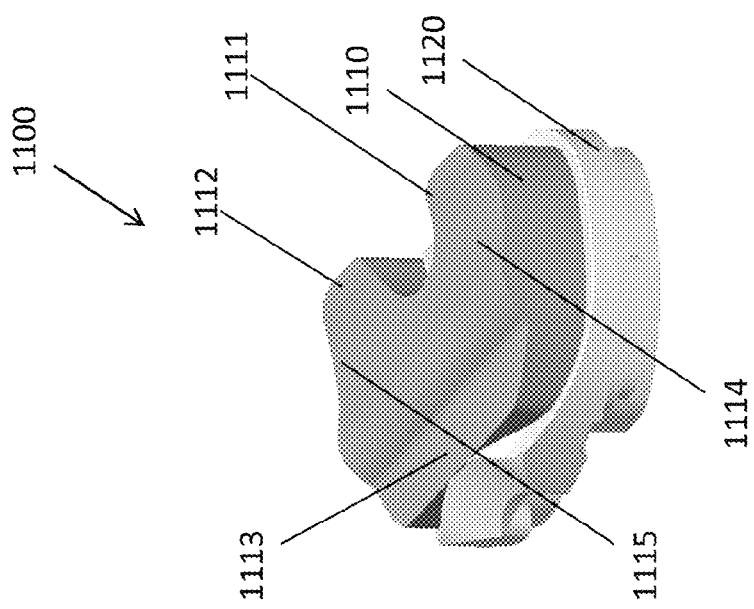

It may also be desirable to have a single tibial trial 1100 that can be used with a distal femur 100 (with or without shims) resected according to a preliminary resection profile 150 and also with after the final cuts have been performed. FIGS. 16A-B illustrate such a tibial trial 1100. Tibial trial 1100 includes a first insert 1110 and a second insert 1120. First insert 1110 takes a similar form to certain embodiments described above. For example, first insert 1110 may include a first condylar portion 1111 and a second condylar portion 1112 connected by a bridge 1113 at anterior ends of the first and second condylar portions. A proximal surface of the first condylar portion 1111 may include a sulcus or groove 1114 and a proximal surface of the second condylar portion 1112 may also include a sulcus or groove 1115. As described above, each groove 1114, 1115 may be configured to correspond with the dished plateaus of the tibial implant and provide articulation with the machined surface of the distal femur 100 after it is resected according to the curved resection profile. The distal surface of the first insert 1110 may include pegs 1116, 1116 configured to be inserted in corresponding holes in 1126, 1127 in the second insert 1120.

The second insert 1120 may also have a first condylar portion 1121 and a second condylar portion 1122 connected by a bridge 1123 at anterior ends of the first and second condylar portions. The proximal surface of the second insert 1120 may take a traditional shape capable of articulating with the distal femur 100 after a final cut has been made following intraoperative trialing with the first insert 1100. Tibial trial 1100 allows a surgeon to dynamically trial the distal femur 100 that has been resected according to the preliminary resection profile 150. The surgeon may then, when satisfied, perform the final cuts. After performing the final cuts, the surgeon may remove the first insert 1110 from first trial 1100, leaving the more traditional surface of second trial 1120 available for standard trialing.

Figure 17B:
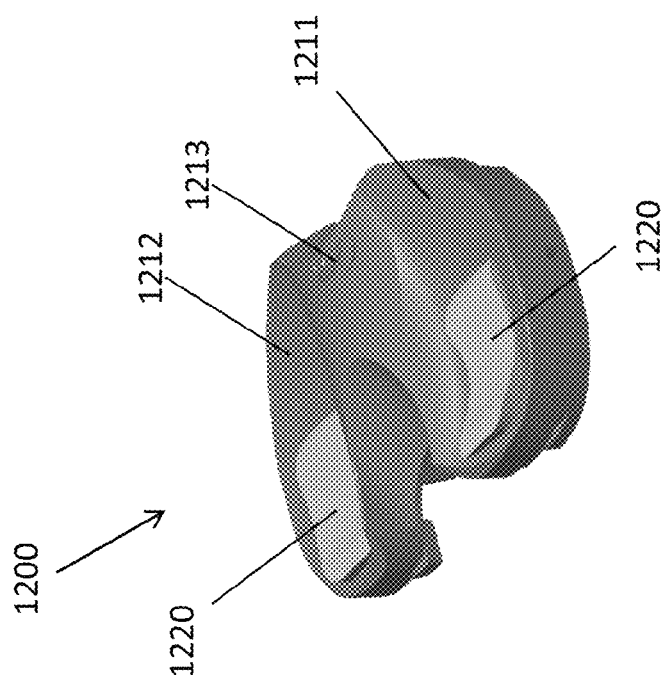
FIGS. 17A-B illustrate perspective views of another dual-use tibial trial according to an aspect of the disclosure.
Figure 17A:
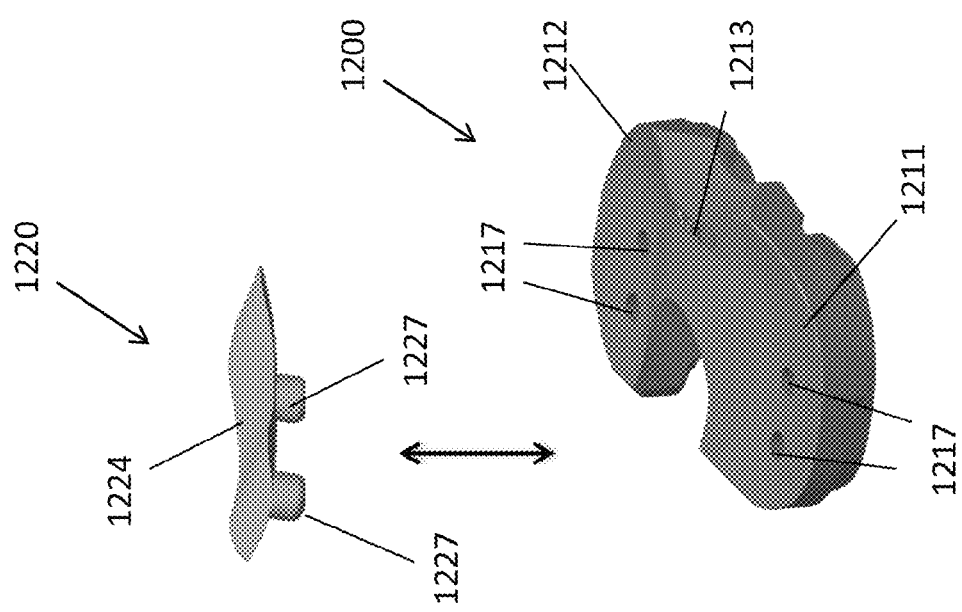

Another insert 1200 capable of dual use is illustrated in FIGS. 17A-B. Insert 1200 may include a first condylar portion 1211 and a second condylar portion 1212 connected by a bridge 1213 at anterior ends of the first and second condylar portions. The proximal surface of the first and second condylar portions 1211, 1212 are configured to articulate with the distal femur 100 according to standard trialing methods after a final cut has been performed on the femur. However, first condylar portion 1211 includes two holes 1216 and second condylar portion 1212 includes two holes 1217. Holes 1216, 1217 are configured to accept pegs 1227 of a sulcus insert or groove insert 1220 (only one groove insert illustrated in FIG. 17A). Each groove insert 1220 includes a sulcus or groove 1224 on an articulation surface thereof. When used without groove inserts 1220, insert 1200 may perform as more traditional trial inserts do. However, if the surgeon prefers to dynamically trial the distal femur 100 after performing a preliminary resection according to the preliminary resection profile 150, a groove insert 1220 may be attached to each of the first and second condylar portions 1211, 1212 of the insert 1200, providing a surface that may articulate directly with the machined surface of the distal femur. As should be appreciated, insert 1200 provides a surgeon the ability to dynamically trial the femur 100 following a preliminary resection when the groove inserts 1220 are attached, and then perform final cuts to the femur and then perform standard trialing after removing the groove inserts 1220 from the trial insert 1200.

In an exemplary knee replacement procedure, such as a cruciate retaining ("CR") TKA, the surgeon may begin by creating an incision at the surgical site and mounting anatomy trackers, such as femoral or tibial trackers. The bones are registered to allow a guidance system to track the position of the bones during the procedure. A navigation system with a GUI and other components known in the art may be used to verify the registration and the planned implant position. At this point, the surgeon may perform an initial kinematic analysis of the knee including, for example, analysis of the pre-operative implant positions, checking the implant design plan against actual bone overlap, and checking flexion and extension gaps. The surgeon may, if satisfied, verify the operative plan and begin the procedure. Following this initial kinematic analysis, if performed, the surgeon may position the machining robot and apply retractors to the incision in preparation of machining the bone.

The robot may perform the preliminary bone resection of the distal femur 100 and proximal tibia 200 using, for example, a large barrel bur, such as a 6, 8 or 10 mm bur. However, other machining tools and other size burs may be used, and the examples provided are meant only to be illustrative. The same bur may also be used to perform the preliminary machining of both the distal femur 100 and the proximal tibia 200, if desired. The distal femur 100 and proximal tibia 200 may also be machined simultaneously. As described above in relation to FIGS. 1-4D, a preliminary bone resection may be performed on the distal femur according to the preliminary resection profile 150, such as the curved resection profile, while a preliminary bone resection may be performed on the proximal tibia according to a separate preliminary resection profile 250. Having been described previously, the particular details of the preliminary resection profiles 150, 250 are not repeated here.

After the preliminary bone resection is complete for both the distal femur 100 and the proximal tibia 200, intraoperative trialing, including kinematic analysis and gap balancing, may be performed. To perform the intraoperative trailing and gap analysis, the surgeon chooses a desired trial component. The particular trial component may be a component described herein or any other suitable component. If trialing the machined distal femur 100 according to the curved resection profile corresponding to a "single radius" femoral implant 180, a trial insert designed for use with the native resected femur, such as one with a sulcus or groove for each condyle, is preferred. However, as described above, other preliminary resection profiles, including a planar resection profile, may be implemented for other types of femoral implants, in which a flexion axis is derived from the particular implant and a preliminary femoral resection is made. The geometry of the preliminary femoral bone resection with other apparatus, such as shims 400, corresponds to the geometry of the femoral implant such that intraoperative trailing is indicative of the kinematics of the implant system according to the final design plan. In these cases, it may be desirable to perform the intraoperative trialing with a more traditional component, including certain embodiments described herein. The surgeon may perform a second kinematic analysis including gap balancing at a range of angles of flexion and extension, as described above with reference to FIGS. 7A-B. If the values determined from kinematic analysis meet the surgeon's targets, he may continue to the next step. If the values do not meet the surgeon's targets, he may take corrective action, such as releasing soft tissue, changing the planned position of the implant, or performing a second machining step to further resect the bone. These steps may be performed in an iterative fashion, fine tuning the bone, tissue, and final implant position for an optimal result. This may be possible, in part, to the remaining bone stock, at approximately 2 mm to approximately 3 mm, as the surgeon may still reshape the remaining bone stock as desired. Preferably, the surgeon will be able to perform this fine tuning up with a variation up to between approximately 2 mm and approximately 3 mm (translational) and up to approximately 2 degrees (angular) from the original final design plan.

After the surgeon is satisfied with the second kinematic analysis, any intraoperative gap balancing performed, and any revisions to the preoperative plan, the distal femur 100 and proximal tibia 200 may be finished. The robot may finish the distal femur 100 according to the final projected femoral cut plan 170, or a modified plan if the femoral cut plan 170 was modified by the surgeon as a result of the second kinematic analysis and/or intraoperative gap balancing. Similarly, the robot may finish the proximal tibia 200 according to the final projected tibial cut plan 270, or a modified plan if the projected tibial cut plan 270 has been modified by the surgeon.

After the finishing cuts are made to the distal femur 100 and proximal tibia 200, the surgeon may perform traditional trial reduction and analysis, as is known in the art, along with a third kinematic analysis. If a dual use trial insert was used for the dynamic trialing, such as those described in relation to FIGS. 16A-B and 17A-B, the surgeon may simply modify the insert as described so that it may be used again in its modified form for this stage of trialing. At this stage, the surgeon may make any final adjustments deemed necessary and implant the femoral implant 180 onto the distal femur 100 and the tibial implant 280 onto the proximal tibia 200. The surgeon may perform a fourth and final kinematic analysis to assess the final positions of the implants 180, 280.

It should be noted that, although trialing and kinematic analysis has generally been discussed in relation to the tibia and femur, the dynamic trialing may also assist in optimizing patellar tracking, placement, and extensor mechanism tightness. This is because, at least in part, dynamic trialing may involve the kinematics of the entire joint, of which the patella is a part.

As should be appreciated, performing a knee replacement according to the above description provides the surgeon the ability to fine tune the preoperative plan while simultaneously reducing complexity, cost, and operation time compared to previously known methods and apparatus.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, the principles described herein may be applicable to other joint procedures including, for example, hip arthroplasty.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A dynamic trialing method comprising:
creating a bone model of a distal femur of a patient;
determining a preliminary curved resection profile on the bone model offset from distal and posterior nonresected articular surfaces of the distal femur;
determining a final desired resection profile prior to making a preliminary resection, the determined final desired resection profile being based at least in part on a planned resection of a bone surface of the preliminary curved resection profile;
resecting the distal femur by making the preliminary resection along the preliminary curved resection profile such that a first area of bone is removed from the distal femur;
engaging the resected distal femur to a tibial trial coupled to a resected proximal tibia; and
performing intraoperative kinematic analysis by at least articulating the proximal tibia with respect to the distal femur.

2. The dynamic trialing method of claim 1, wherein the step of performing kinematic analysis further includes performing intraoperative gap balancing.

3. The dynamic trialing method of claim 2, further comprising:
making a subsequent resection of the distal femur such that a second area of bone is removed from the distal femur.

4. The dynamic trialing method of claim 3, wherein the subsequent resection includes making planar bone resections corresponding to mating surfaces on a femoral implant.

5. The dynamic trialing method of claim 3, wherein the subsequent resection is performed according to the final desired resection profile.

6. The dynamic trialing method of claim 3, wherein the subsequent resection is performed according to a modified final section profile, the modified final section profile being determined, at least in part, based upon results of the kinematic analysis.

7. The dynamic trialing method of claim 1, wherein the tibial trial includes a first condylar portion connected to a second condylar portion, the first and second condylar portions each having a groove corresponding to an articular dish of a tibial implant plateau.

8. The dynamic trialing method of claim 7, wherein the tibial trial includes a tibial trial insert and a template, the tibial trial insert being removable from the template.

9. The dynamic trialing method of claim 8, further comprising the step of removing the tibial trial insert from the template and inserting an alternative modular tibial trial insert into the template.

10. The dynamic trialing method of claim 7, wherein the tibial trial includes a first insert having a proximal surface and a distal surface and a second insert having a proximal surface, the proximal surface of the first insert having two grooves corresponding to articular dishes of the tibial implant plateau.

11. The dynamic trialing method of claim 10, wherein the first insert has at least two pegs extending distally from the distal surface of the first insert and the second insert has at least two holes on the proximal surface of the second insert, the at least two pegs being configured to be inserted into the at least two holes.

12. The dynamic trialing method of claim 7, wherein the tibial trial includes a tibial insert having a first condylar portion configured to mate with a first groove insert and a second condylar portion configured to mate with a second groove insert, the first and second groove inserts each having an articulation surface corresponding to the articular dish of the tibial implant plateau.

13. The dynamic trialing method of claim 1, further comprising the step of coupling first and second femoral shims to first and second condyles of the distal femur after the step of resecting the distal femur by making a preliminary resection.

14. The dynamic trialing method of claim 13, wherein the first and second femoral shims each have an articulation surface corresponding to a shape of a femoral implant.

15. The dynamic trialing method of claim 14, wherein the first and second femoral shims each have a bone contacting surface with a peg extending therefrom, the pegs being configured to facilitate fixing the first and second femoral shims to the resected distal femur.

16. The dynamic trialing method of claim 1, wherein the tibial trial includes a first condylar portion, a second condylar portion, and at least one insert surface, the at least one insert surface being connected to at least one expandable component having a volume that may expand or contract and also being configured to remain at a constant pressure.

17. The dynamic trialing method of claim 16, wherein the tibial trial has exactly one insert surface and exactly one expandable component, the first and second condylar portions being connected to one another.

18. The dynamic trialing method of claim 16, wherein the tibial trial has two insert surfaces and two expandable components, a first insert surface corresponding to a first expandable component and the first condylar portion, and a second insert surface corresponding to a second expandable component and a second condylar portion.

19. The dynamic trialing method of claim 18, wherein the tibial trial includes a connecting member physically connecting the first condylar portion to the second condylar portion, the first expandable portion being fluidly isolated from the second expandable portion.

20. The dynamic trialing method of claim 16, wherein the at least one expandable component is a bellows.

21. The dynamic trialing method of claim 20, wherein the at least one expandable component is connected to a fluid source.

22. The dynamic trialing method of claim 21, wherein the fluid source is configured to pump air into the at least one expandable component.

23. The dynamic trialing method of claim 21, wherein the fluid source is configured to pump saline into the at least one expandable component.

24. A dynamic trialing method comprising:
creating a bone model of a distal femur of a patient;
determining a preliminary resection profile on the bone model;
determining a final desired resection profile prior to making a preliminary resection, the determined final desired resection profile being based at least in part on a planned resection of a bone surface of the preliminary resection profile; and
resecting the distal femur by making the preliminary resection along the preliminary resection profile such that a first area of bone is removed from the distal femur,
wherein the preliminary resection profile is determined, at least in part, based on a feature of a final design plan of a femoral implant.

25. The dynamic trialing method of claim 24, wherein the final design plan of the femoral implant includes a femoral implant flexion axis, and the preliminary resection profile is based on the femoral implant flexion axis.

26. The dynamic trialing method of claim 25, wherein the preliminary resection profile includes a flexion axis, the flexion axis of the preliminary resection profile being coaxial with the femoral implant flexion axis.

27. The dynamic trialing method of claim 24, further comprising the step of performing intraoperative kinematic analysis by at least articulating the proximal tibia with respect to the distal femur.

28. The dynamic trialing method of claim 27, further comprising the step of performing intraoperative gap balancing.

* * * * *